US012396986B2

(12) United States Patent
Baker et al.

(10) Patent No.: US 12,396,986 B2
(45) Date of Patent: *Aug. 26, 2025

(54) COMBINATIONS OF A MUSCARINIC RECEPTOR ANTAGONIST AND A β-2 ADRENORECEPTOR AGONIST

(71) Applicant: Glaxo Group Limited, Stevenage (GB)

(72) Inventors: Darrell Baker, Uxbridge (GB); Mark Bruce, Stevenage (GB); Glenn Crater, Mississauga (CA); Brian Noga, Durham, NC (US); Marian Thomas, Ware (GB); Patrick Wire, Durham, NC (US)

(73) Assignee: Glaxo Group Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/485,799

(22) Filed: Oct. 12, 2023

(65) Prior Publication Data
US 2024/0041846 A1 Feb. 8, 2024

Related U.S. Application Data

(60) Continuation of application No. 17/514,685, filed on Oct. 29, 2021, now abandoned, which is a continuation of application No. 16/781,587, filed on Feb. 4, 2020, now abandoned, which is a continuation of application No. 15/678,246, filed on Aug. 16, 2017, now Pat. No. 11,090,294, which is a division of application No. 14/970,945, filed on Dec. 16, 2015, now Pat. No. 9,750,726, which is a continuation of application No. 13/510,962, filed as application No. PCT/EP2010/068429 on Nov. 29, 2010, now abandoned.

(30) Foreign Application Priority Data

Dec. 1, 2009 (GB) ..................... 0921075

(51) Int. Cl.
A01N 43/00 (2006.01)
A61K 9/00 (2006.01)
A61K 31/138 (2006.01)
A61K 31/33 (2006.01)
A61K 31/439 (2006.01)
A61K 31/7052 (2006.01)
A61K 45/06 (2006.01)
A61P 31/04 (2006.01)
B65D 75/36 (2006.01)
C07H 15/203 (2006.01)
C07H 15/26 (2006.01)

(52) U.S. Cl.
CPC .......... A61K 31/439 (2013.01); A61K 9/0075 (2013.01); A61K 31/138 (2013.01); A61K 31/7052 (2013.01); A61K 45/06 (2013.01); A61P 31/04 (2018.01); B65D 75/36 (2013.01); C07H 15/203 (2013.01); C07H 15/26 (2013.01)

(58) Field of Classification Search
CPC .............. A61K 2300/00; A61K 31/138; A61K 31/439; A61K 31/7052; A61K 45/06; A61K 9/0075; A61P 11/00; A61P 11/02; A61P 11/06; A61P 11/08; A61P 29/00; A61P 31/04; A61P 37/08; A61P 43/00; C07H 15/203; C07H 15/26; B65D 75/36; Y02A 50/30

See application file for complete search history.

(56) References Cited

U.S. PATENT DOCUMENTS

| | | |
|---|---|---|
| 4,778,054 A | 10/1988 | Newell |
| 4,811,731 A | 3/1989 | Newell et al. |
| 4,832,880 A | 5/1989 | Staniforth |
| 4,994,276 A | 2/1991 | Baichwal et al. |
| 5,004,614 A | 4/1991 | Staniforth |
| 5,035,237 A | 7/1991 | Newell et al. |
| 5,135,757 A | 8/1992 | Baichwal et al. |
| 5,145,684 A | 9/1992 | Liversidge et al. |
| 5,376,386 A | 12/1994 | Ganderton et al. |
| 5,441,060 A | 8/1995 | Rose et al. |
| 5,478,578 A | 12/1995 | Arnold et al. |
| 5,503,662 A | 4/1996 | Berger |
| 5,506,203 A | 4/1996 | Backstrom et al. |
| 5,560,490 A | 10/1996 | Chawla |
| 5,590,645 A | 1/1997 | Davies et al. |
| 5,626,871 A | 5/1997 | Makino et al. |
| 5,642,728 A | 7/1997 | Anderson et al. |
| 5,663,198 A | 9/1997 | Reul et al. |
| 5,730,785 A | 3/1998 | Idol et al. |
| 5,746,937 A | 5/1998 | McKedy et al. |
| 5,829,434 A | 11/1998 | Ambrosio et al. |

(Continued)

FOREIGN PATENT DOCUMENTS

| | | |
|---|---|---|
| CA | 2347856 C | 5/2000 |
| DE | 202005002409 U1 | 6/2005 |

(Continued)

OTHER PUBLICATIONS

Jonathan Robert Caronia, Restrictive lung disease, Oct. 31, 2016 (Year: 2016).*

(Continued)

Primary Examiner — Jean P Cornet
(74) Attorney, Agent, or Firm — J. Scott Young

(57) ABSTRACT

Combinations of a muscarinic acetylcholine receptor antagonist and a beta 2 agonist for inhaled administration via the nose or mouth, compositions thereof, and methods of using them are provided.

56 Claims, No Drawings

(56) References Cited

U.S. PATENT DOCUMENTS

| | | | |
|---|---|---|---|
| 5,860,419 | A | 1/1999 | Davies et al. |
| 5,873,360 | A | 2/1999 | Davies et al. |
| 5,972,388 | A | 10/1999 | Sakon et al. |
| 6,032,666 | A | 3/2000 | Davies et al. |
| 6,103,141 | A | 8/2000 | Incorvia et al. |
| 6,119,853 | A | 9/2000 | Garrill et al. |
| 6,132,394 | A | 10/2000 | Lankinen |
| 6,153,224 | A | 11/2000 | Staniforth |
| 6,153,322 | A | 11/2000 | Lee et al. |
| 6,156,231 | A | 12/2000 | McKedy et al. |
| 6,179,118 | B1 | 1/2001 | Garrill et al. |
| D440,874 | S | 4/2001 | Shurtleff et al. |
| 6,221,338 | B1 | 4/2001 | Staniforth |
| 6,279,736 | B1 | 8/2001 | Hekal |
| 6,315,112 | B1 | 11/2001 | Garrill et al. |
| 6,321,747 | B1 | 11/2001 | Dmitrovic et al. |
| 6,352,152 | B1 | 3/2002 | Amderson et al. |
| 6,378,519 | B1 | 4/2002 | Davies et al. |
| 6,378,579 | B1 | 4/2002 | Giltner |
| 6,390,291 | B1 | 5/2002 | Garrill et al. |
| 6,521,260 | B1 | 2/2003 | Staniforth |
| 6,533,321 | B2 | 3/2003 | Class et al. |
| 6,536,427 | B2 | 3/2003 | Biggadike et al. |
| 6,537,983 | B1 | 3/2003 | Biggadike et al. |
| 6,582,678 | B2 | 6/2003 | Staniforth |
| 6,679,374 | B2 | 1/2004 | Garrill et al. |
| 6,759,398 | B2 | 7/2004 | Biggadike et al. |
| 6,792,945 | B2 | 9/2004 | Davies et al. |
| 6,878,698 | B2 | 4/2005 | Biggadike et al. |
| 7,011,818 | B2 | 3/2006 | Staniforth |
| 7,101,866 | B2 | 9/2006 | Biggadike et al. |
| 7,186,401 | B2 | 3/2007 | Keller et al. |
| 7,225,808 | B2 | 6/2007 | Davies et al. |
| 7,337,593 | B2 | 3/2008 | Blum et al. |
| 7,361,787 | B2 | 4/2008 | Box et al. |
| 7,389,775 | B2 | 6/2008 | Davies et al. |
| 7,439,393 | B2 | 10/2008 | Box et al. |
| 7,488,827 | B2 | 2/2009 | Laine et al. |
| 7,498,440 | B2 | 3/2009 | Laine et al. |
| 7,501,011 | B2 | 3/2009 | Powers et al. |
| 7,549,272 | B2 | 6/2009 | DeFedericis |
| 7,629,335 | B2 | 12/2009 | Biggadike et al. |
| 7,776,895 | B2 | 8/2010 | Box et al. |
| 7,982,067 | B2 | 7/2011 | Box et al. |
| 8,183,257 | B2 | 5/2012 | Aine et al. |
| 8,303,991 | B2 | 11/2012 | Staniforth et al. |
| 8,309,572 | B2 | 11/2012 | Laine et al. |
| 8,511,304 | B2 | 8/2013 | Anderson et al. |
| RE44,874 | E | 4/2014 | Box et al. |
| 9,365,905 | B2 | 6/2016 | Newman et al. |
| 9,750,726 | B2 | 9/2017 | Baker et al. |
| 2003/0026766 | A1 | 2/2003 | Sanders |
| 2005/0121027 | A1 | 6/2005 | Nilsson et al. |
| 2005/0124644 | A1 | 6/2005 | Nilsson et al. |
| 2006/0134007 | A1 | 6/2006 | Krueger et al. |
| 2006/0144733 | A1 | 7/2006 | Wu et al. |
| 2006/0239932 | A1 | 10/2006 | Monteith et al. |
| 2006/0239933 | A1 | 10/2006 | Nilsson et al. |
| 2006/0257327 | A1 | 11/2006 | Zierenberg et al. |
| 2006/0269708 | A1 | 11/2006 | Merical et al. |
| 2007/0088030 | A1 | 4/2007 | Niklaus-Humke et al. |
| 2007/0104655 | A1 | 5/2007 | Zierenberg et al. |
| 2007/0110678 | A1 | 5/2007 | Zierenberg et al. |
| 2007/0164254 | A1 | 7/2007 | Powers et al. |
| 2007/0212422 | A1 | 9/2007 | Keller et al. |
| 2008/0003290 | A1 | 1/2008 | Box et al. |
| 2008/0063719 | A1 | 3/2008 | Morton et al. |
| 2009/0013998 | A1 | 1/2009 | Nilsson et al. |
| 2009/0029901 | A1 | 1/2009 | Wood-Kaczmar |
| 2009/0041682 | A1 | 2/2009 | Nilsson et al. |
| 2009/0152155 | A1 | 6/2009 | Pasbrig |
| 2009/0188495 | A1 | 7/2009 | Nilsson et al. |
| 2009/0192185 | A1 | 7/2009 | Nilsson et al. |
| 2009/0234929 | A1 | 9/2009 | Matsumoto |
| 2009/0298742 | A1 | 12/2009 | Roche et al. |
| 2011/0017615 | A1 | 1/2011 | Logel et al. |
| 2011/0269970 | A1 | 11/2011 | Box et al. |
| 2012/0309725 | A1 | 12/2012 | Baker et al. |
| 2014/0113888 | A1 | 4/2014 | Crater |
| 2015/0313841 | A1 | 11/2015 | Jones |
| 2016/0095840 | A1 | 4/2016 | Baker et al. |

FOREIGN PATENT DOCUMENTS

| | | | |
|---|---|---|---|
| DE | 202005004659 | U1 | 8/2005 |
| DE | 10056855 | A1 | 11/2010 |
| EP | 0069715 | A | 1/1983 |
| EP | 0239798 | B1 | 9/1990 |
| EP | 466068 | A2 | 1/1992 |
| EP | 0328685 | B1 | 5/1992 |
| EP | 0824480 | B1 | 2/1998 |
| EP | 0606486 | B1 | 8/2001 |
| EP | 1240261 | B1 | 9/2002 |
| EP | 1241110 | A1 | 9/2002 |
| EP | 1243524 | A2 | 9/2002 |
| EP | 1131059 | B1 | 3/2003 |
| EP | 1292510 | B1 | 3/2003 |
| EP | 1626913 | B1 | 12/2004 |
| EP | 1827283 | B1 | 6/2006 |
| EP | 1691783 | A1 | 8/2006 |
| EP | 1883400 | B1 | 11/2006 |
| EP | 1232745 | B1 | 3/2007 |
| EP | 1990052 | A1 | 8/2007 |
| EP | 1991292 | A1 | 11/2008 |
| EP | 2127628 | A1 | 12/2009 |
| EP | 2277799 | A1 | 1/2011 |
| EP | 2283817 | | 2/2011 |
| EP | 2283818 | | 2/2011 |
| EP | 2954888 | A1 | 12/2015 |
| FR | 2660634 | A1 | 10/1991 |
| GB | 124009 | | 3/1919 |
| GB | 124010 | | 3/1919 |
| GB | 1242211 | A | 8/1971 |
| GB | 1381872 | | 1/1975 |
| GB | 1424432 | | 2/1976 |
| GB | 2064336 | A | 6/1981 |
| GB | 2129691 | A | 5/1984 |
| GB | 2178965 | A | 2/1987 |
| GB | 2242134 | A | 9/1991 |
| GB | 2269992 | A | 3/1994 |
| GB | 2169265 | A | 7/1996 |
| GB | 2410192 | A | 7/2005 |
| JP | 2002532216 | A | 10/2002 |
| WO | 198705213 | A1 | 9/1987 |
| WO | 93/11746 | A1 | 6/1993 |
| WO | 199500128 | A1 | 1/1995 |
| WO | 199511666 | A1 | 5/1995 |
| WO | 1995032752 | A1 | 12/1995 |
| WO | 96/19199 | A1 | 6/1996 |
| WO | 199623485 | A1 | 8/1996 |
| WO | 97/03649 | A1 | 2/1997 |
| WO | 99/38493 | A1 | 8/1999 |
| WO | 1999040031 | A2 | 8/1999 |
| WO | 99/53901 | A1 | 10/1999 |
| WO | 00/27363 | A1 | 5/2000 |
| WO | 2000028979 | A1 | 5/2000 |
| WO | 00/33811 | A1 | 6/2000 |
| WO | 2000037336 | A1 | 6/2000 |
| WO | 00/53157 | A1 | 9/2000 |
| WO | 00/53158 | A1 | 9/2000 |
| WO | 01/76575 | A2 | 10/2001 |
| WO | 01/78694 | A2 | 10/2001 |
| WO | 2001087731 | A2 | 11/2001 |
| WO | 2001097888 | A2 | 12/2001 |
| WO | 2001098174 | A1 | 12/2001 |
| WO | 02/43700 | A2 | 6/2002 |
| WO | 2002098874 | A2 | 12/2002 |
| WO | 2003024439 | A1 | 3/2003 |
| WO | 2003057593 | A1 | 7/2003 |
| WO | 2003061743 | A1 | 7/2003 |
| WO | 2004000541 | A1 | 12/2003 |
| WO | 2004080808 | A2 | 9/2004 |
| WO | 2004101390 | A1 | 11/2004 |
| WO | 2004105727 | A2 | 12/2004 |

(56) References Cited

FOREIGN PATENT DOCUMENTS

| | | |
|---|---|---|
| WO | 2004110404 A1 | 12/2004 |
| WO | 2005004845 A1 | 1/2005 |
| WO | 2005004848 A1 | 1/2005 |
| WO | 2005004853 A1 | 1/2005 |
| WO | 2005037280 A1 | 4/2005 |
| WO | 2005040304 A1 | 5/2005 |
| WO | 2005044186 A2 | 5/2005 |
| WO | 2005046636 A1 | 5/2005 |
| WO | 2005053644 A1 | 6/2005 |
| WO | 2005053645 A1 | 6/2005 |
| WO | 2005053646 A1 | 6/2005 |
| WO | 2005053647 A1 | 6/2005 |
| WO | 2005053648 A1 | 6/2005 |
| WO | 2005104745 A2 | 11/2005 |
| WO | 2005115462 A1 | 12/2005 |
| WO | 2005115463 A1 | 12/2005 |
| WO | 2005115464 A1 | 12/2005 |
| WO | 2005115465 A1 | 12/2005 |
| WO | 2005115466 A1 | 12/2005 |
| WO | 2005115467 A1 | 12/2005 |
| WO | 2005123002 A1 | 12/2005 |
| WO | 2006000758 A1 | 1/2006 |
| WO | 2006008173 A2 | 1/2006 |
| WO | 2006023457 A1 | 3/2006 |
| WO | 2006045715 A1 | 5/2006 |
| WO | 2006062883 A2 | 6/2006 |
| WO | 2006062931 A2 | 6/2006 |
| WO | 2006071844 A2 | 7/2006 |
| WO | 2006108572 A2 | 10/2006 |
| WO | 2006115264 A1 | 11/2006 |
| WO | 2006124556 A2 | 11/2006 |
| WO | 2006135474 A1 | 12/2006 |
| WO | 2007012871 A1 | 2/2007 |
| WO | 2007037748 A1 | 4/2007 |
| WO | 2007042822 A2 | 4/2007 |
| WO | 2007045378 A2 | 4/2007 |
| WO | 2007057081 A1 | 5/2007 |
| WO | 2007068896 A1 | 6/2007 |
| WO | 2007097451 A1 | 8/2007 |
| WO | 2007102635 A1 | 9/2007 |
| WO | 2007109606 A2 | 9/2007 |
| WO | 2007109698 A2 | 9/2007 |
| WO | 2007109824 A1 | 10/2007 |
| WO | 2007117911 A | 10/2007 |
| WO | 2007121259 A2 | 10/2007 |
| WO | 2007135024 A1 | 11/2007 |
| WO | 2008012338 A2 | 1/2008 |
| WO | 2008014862 A1 | 2/2008 |
| WO | 2008021142 A2 | 2/2008 |
| WO | 2008040841 A1 | 4/2008 |
| WO | 2008049842 A2 | 5/2008 |
| WO | 2008091968 A1 | 7/2008 |
| WO | 2008121321 A1 | 10/2008 |
| WO | 2008135570 A1 | 11/2008 |
| WO | 2009013243 A1 | 1/2009 |
| WO | 2009013244 A1 | 1/2009 |
| WO | 2009029029 A1 | 3/2009 |
| WO | 2009036243 A1 | 3/2009 |
| WO | 2009090010 A1 | 7/2009 |
| WO | 2009103336 A1 | 8/2009 |
| WO | 2009155387 A2 | 12/2009 |
| WO | 2010038086 A2 | 4/2010 |
| WO | 2010072354 A1 | 7/2010 |
| WO | 2010097114 A1 | 9/2010 |
| WO | 2010097115 A1 | 9/2010 |
| WO | 2010135340 A2 | 11/2010 |
| WO | 2011067212 A1 | 6/2011 |
| WO | 2012168160 A1 | 12/2012 |
| WO | 2012168161 A1 | 12/2012 |

OTHER PUBLICATIONS

CCFA, Treatment Options in IBD (inflammatory bowel disease), May 30, 2012 teaches (Year: 2012).*
Webb et al., Can Vet J. Sep. 2002; 43(9): 703-705 (Year: 2002).*
Bhatti et al., Ann Thorac Med. Apr.-Jun. 2013; 8(2): 71-77 (Year: 2013).*
541024, RD, May 10, 2009.
FDA Guidance Metered Dose Inhaler (MDI) and Dry Powder Inhaler (DPI) Drug Products, Nov. 13, 1998; Chemistry, Manufacturing and Controls Documentations.
FDA Pulmonary Allergy Drugs Advisory Committee Meeting, Feb. 23, 2012, NOA 202-450: aclidinium bromide for the long-term, maintenance treatment of bronchospasm associated with chronic obstructive pulmonary disease (COPD), including chronic bronchitis and emphysema. (UMC292620). Retrieved from: https://www.fda.gov/downloads/AdvisoryCommittees/CommitteesMeetingMaterials/Drugs/Pulmonary-AllergyDrugsAdvisoryCommittee/UCM292620.pdf.
FDA, U.S. Food & Drug Administration, TUDORZA™ PRESSAIR™—US FDA Approved Product Label. Retrieved Online at: http://www.accessdata.fda.gov/scripts/cder/daf/index.cfm?event=BasicSearch.process (2012).
Fee, et al., "Influence of hydrophobic materials on dissolution of a nondisintegrating hydrophilic solid (potassium chloride)" JPharmSci; 1976; pp. 182-187; vol. 65.
Fierce Biotech News Release: GSK and Theravance announce positive phase 2b results for LABA, '444 in the Horizon Asthma Development programme, dated Dec. 2, 2008.
Ford, et al., "The therapeutic index of vilanterol trifenatate." Eur. Respir. J.; 2010; vol. 36, Suppl. 54: pp. 1184.
Forest Pharmaceuticals, Highlights of Prescribing Information, Tudorza Pressair. (2012).
Ganderton, "The Generation of Respirable Clouds Form Coarse Powder Aggregates" 1992; Journal of Biopharmaceutical Sciences; vol. 3 (1/2); pp. 101-105.
Cazzola, et al., "Novel Long-acting bronchodilators for COPD and asthma." Brit J Pharm; 2008; pp. 291-299; vol. 155.
GJE Notice of Opposition to European patent No. 2400950 to Glaxo Group Limited dated Feb. 20, 2020.
Global Initiative for the Diagnosis, Management and Prevention of Chronic Obstructive Pulmonary Disease, p. 14 2016).
GlaxoSmithKline, Evaluate the Safety, Efficacy and Dose Response of GSK573719 in Combination With Fluticasone Furoate in Subjects With Asthma {ILA115938). ClinicalTrials.gov Identifier NCT01573624, First Received Apr. 5, 2012, retrieved online at: https://clinicaltrials.gov/cl2/show/NCT01573624.
Glaxosmithkline, Highlights of Prescribing Information, Anoro Ellipta, FDA NDA 203975s003. (2016).
GSK Annual Report, retrieved online at: http://annualreport.gsk.com/ (2015).
GSK Clinical Trial No. NCT01128569, Randomised Study Comparing the Effects of Inhaled Fluticasone Furoate (FF)/ Vilanterol (VI; GW642444M) Combination and FF on an Allergen Induced Asthmatic Response, https://clinicaltrials.gov/ct2/show/study/NCT01128569?TERM=gw+642444m+fluticasone&rank=4; First received May 20, 2010; Last updated May 29, 2014; pp. 1-5.
GlaxoSmithKline commences Relovair Phase III asthma programme; https://us/gsk.com/en-us/media/press-releases/2010/glaxosmithkline-commences-reloviar-phase-III-asthma-programme/; Dec. 17, 2015; pp. 1-13.
Guchardi et al., International Journal of Pharmaceutics, vol. 348, Issues 1-2, Feb. 4, 2008, pp. 10-17.
Guidance for Industry, "Metered dose inhaler (MDI) and dry powder inhaler (DPI) drug products, chemistry, manufacturing, and cold pulse documentation, graft guldance", US Department of Health and Human Services, Food and Drug Administration, Center for Drug Evaluation and Research (CDER), Oct. 1998.
Hajdu, D., et al., "Molecular Seives: Unique Moisture and Odor-Taste Control Material," Aug. 22-26, 1999; TAPPI Polymers, Laminations & Coatings Conference; Atlanta, vol. 2; pp. 655-662 (Abstract).
Hanania, et al., The Efficacy and Safety of the Novel Long-Acting B2 Agonist Vilanterol in Patients with COPD; Jul. 1, 2012; Chest; vol. 142; pp. 119-127.
Hanania, et al., "Safety of vilanterol trifenatate (VI) in a COPD dose-ranging study," Eur Respir J; 2010; vol. 36, Suppl, 54; pp. 1185.

(56) References Cited

OTHER PUBLICATIONS

HygroPalm HP23-A/HP23-AW-A-Hand-Held Indicator User Guide, Rotronic AG; 2009-2012; pp. 1-39.
ICH Topic E 4 Dose Response Information to Support Drug Registration; European Medicines Agency; Nov. 1994.
Jashnani, et al., "Testing of dry powder aerosol formulations in different environmental conditions" International Journal of Pharmaceuticals; 1995; vol. 113; pp. 123-130.
Jashnani et al., "Dry powder aerosol generation in different environments: Performance comparisons of albuterol, albuterol sulfate, albuterol adipate and albuterol stearate", International Journal of Pharmaceutics; 1996; vol. 130; pp. 13-24.
Jones et al., Efficacy and safety of once-daily aclidinium in chronic obstructive pulmonary disease, Respiratory Research (2011), 12:55 http://respiratory-research.com/content/12/1/55.
Jones, P., Aclidinium Bromide Twice Daily for the Treatment of Chronic Obstructive Pulmonary Disease: A Review, Adv. Ther. (2013) , vol. 30, No. 4, pp. 354-368.
Kassem, PhD Thesis "Generation of Deeply Inspirable Clouds from Dry Powder Mixtures" 1990.
Kawashima, et al., Design of inhalation dry powder of pranlukast hydrate to improve dispersibility by the surface modification with light anhydrous silicic acid (AEROSIL 200); Intl J of Pharmaceutics; 1998; pp. 243-251; vol. 173.
Kerwin et al., "A randomised trial of fluticasone furoate/vilanterol (50/25 mcg; 100/25 mcg) on lung function in COPD", Respiratory Medicine, (2013) 107, pp. 560-569.
Laine, D. et al., "Discovery of Novel 1-Azoniabicyclo[2.2.2]octane Muscarinic Acetylcholine Receptor Antagonists" J. Med. Chem. 52(8), 2493-2505 (2009).
Laine, D. et al., "The pre-clinical pharmacology of the inhaled muscarinic antagonist GSK573719 predicts once-daily clinical dosing" Eur. Resp. Socy. vol. 38 Issue Suppl 55 (Sep. 1, 2011).
Lehto, et al., "Moisture Transfer into medicament chambers equipped with a double-barrier-desiccant system", International Journal of Pharmaceutics; 2004; vol. 275 (1/2); 155-164.
Martinez et al., "Effect of Fluticasone Furoate and Vilanterol on Exacerbations of Chronic Obstructive Pulmonary Disease in Patients with Moderate Airflow Obstruction", Am J Respir Crit Care Med, vol. 195, issue 7, pp. 881-888, Apr. 1, 2017.
Martinez et al., "Fluticasone furoate/vilanterol (100/25; 200/25 mcg) improves lung function in COPD: A randomized rial", Respiratory Medicine, (2013), 107, pp. 550-559.
Meakin, et al., "The Effect of Flow Rate on Drug Delivery from the Pulvinal, a High Resistance Dry Powder Inhaler" 1998; Journal of Aerosol Medicine; vol. 11 (3); pp. 143-152.
Multisorb Technologies, "Multisorb Introduces Desiccant Integration Approaches to Preserve the Function of Respiratory Drug Devices and their Drug Product Formulations—New Generation of Multiform Coated Solid Form Sorbents Provide Enhanced Protection for Reservoir Dry Powder"; Jan. 7, 2007: http://multisorb.com/news-andevents/ news/multisorb-introduces-desiccant-integration-approaches-to-preserve-the-function-of-respiratory-drug-devices-and-their-drug-product-formulations-new-generation-of-multiform-coated-solid-form-sorbents-provide-en].
Naito, et al., "Applications of Comminution Techniques for the Surface Modification of Powder Materials" ISIJ International; 1993; pp. 915-924; vol. 33(9).
NIH guidelines on Asthma Treatment; Aug. 28, 2007.
PB62882EP document dated Feb. 14, 2013 re: Response to Communication dated Aug. 9, 2012.
PB62882EP Marked Claims Feb. 2013.
PB62882EP official action dated Aug. 9, 2012.
PB62882EP Unmarked Claims Feb. 2013.
Peart, et al., "Multicomponent Particle Interactions in Dry Powder Aerosols" Nov. 1997; Pharmaceutical Research; Supplement 141; vol. 14 (11); para 1405.
Peters, et al., "Tiotropium Bromide Step-up Therapy for Adults with Uncontrolled Asthma" NE J of Med., 363(18), pp. 1715-1726 (Oct. 28, 2010).

Possumato, Adrian; "New Drug Applications Demand Intelligent Sorbents: Novel formulations and drug-delivery systems require optimized packaging protection"; Pharmaceutical & Medical Packaging News; Oct. 2007.
Ray, Nicholas C. Alcaraz, Lilian. "Muscarinic antagonist-B-adrenergic agonist dual pharmacology molecules as pronchodilators: a patent review". Expert Opin. Ther. Patents (2009) 19 (1): 1-12 published May 1, 2009.
Rosebraugh, Center for Drug Evaluation and Research, Approval Package for: Application No. 203975. Dec. 18, 2013.
"Rule 20.6 PCT Communication with Missing Pages and Drawings" PCT/EP2011/06055, filed Jan. 29, 2013.
Schelfhout et al., Activity of aclidinium bromide, a new long-acting muscarinic antagonist: a phase I study. Br J Clin Pharmacol. May 2010;69(5):458-64.
http://www.pharmpro.com/Archives/2006/10/Harnessing-The-Power-of-Desiccant-Technology-for-Inhalation-Therapies/.
"PCT Application No. PCT/EP2009052306, Notification of Withdrawal of Priority Claim" mailed Aug. 18, 2009.
"Fluticasone", www.Drugs.com, Wolters Kluwer Health (Wayback) (Jun. 4, 2009).
Aaron, S. et al., "Tiotropium in Combination with Placebo, Salmeterol, or Fluticasone-Salmeterol for Treatment of Chronic Obstructive Pulmonary Disease. A Randomized Trial," Annals of Internal Medicine, pp. 545-556, W-144 , vol. 148 (8), Apr. 17, 2007 American College of Physicians.
Advair Diskus® Prescribing Information Aug. 2003.
ADVAIR® HFA Prescribing Information Jun. 2006.
AERA Notice of Opposition to European patent No. 2400950 to Glaxo Group Limited dated Feb. 20, 2020.
Agusti, et al., "A comparison of the efficacy and safety of once-daily fluticasone furoate/vilanterol with twice daily iuticasone propionate/salmeterol in moderate to very severe COPD" Eur Respir J; 2014; vol. 43; pp. 763-772.
Ahmed, PhD. Thesis "Particle Interactions in Multicomponent Systems" 1989.
Allen, A., et al. American Thoracic Society International Conference 2010, Ann Allen et al.: "Fluticasone furoate a hovel inhaled corticosteroid demonstrates prolonged lung absorption kinetics in man" (Abstract).
Allen, A. et al., Fluticasone Furoate, a Novel Inhaled Corticosteroid, Demonstrates Prolonged Lung Absorption Kinetics in Man Compared with Inhaled Fluticasone Propionate Clin Pharmacokinet (on line Nov. 27, 2012); (2013) 52:37-42 print.
Anderson, et al., "A Guide to the Measurement of Humidity", The Institute of Measurement and Control; 1996.
Angberg, M., et al., "Evaluation of heat-conduction microcalorimetry in pharmaceutical stability studies. IV. The influence of microcrystalline cellulose on the hydration rate of anhydrous lactose" 1991; International Journal of Pharmaceutics; vol. 77(2-3); pp. 269-277.
Anonymous, RD541024A, "Package for receiving medical device e.g. dry powder inhaler, has moisture absorbent unit absorbing gaseous and/or liquid substance in puch, where adsorbent unit includes chemically and biologically inert sachet comprising silica gel." May 10, 2009.
Anonymous, "View of NCT01573624 on Apr. 6, 2012" ClinicalTrials. gov; 2012; pp. 1-4.
Arven Opposition to European patent No. 2400950 to Glaxo Group Limited dated Feb. 14, 2020.
Aulton, Michael E., "Pharmaceutics: The science of dosage form design." 1988; pp. 584-590.
Australian Patent Application No. 2011 298 409, Applicant's Response to Examination Report dated Aug. 12, 2013, the response filed Oct. 22, 2013.
Australian Patent Application No. 2011 298 409, Examination Report dated Aug. 12, 2013.
Barnes, "Triple inhalers for obstructive airways disease: Will they be useful?" Expert Review of Respiratory Medicine; 2011; vol. 5(3); pp. 297-300.
Bell, "A Beginner's Guide to Humidity Measurement", National Physical Laboratory; 2011.

(56) References Cited

OTHER PUBLICATIONS

Biggadike, K., "Letter To the Editor, Fluticasone furoate/fluticasone propionate—different drugs with different properties" The Clinical Respiratory Journal 5:3, pp. 183-184 (2011) Print.
Biospace News Release: GlaxoSmithKline and Theravance, Inc. Announce Positive Phase 2b Results for Once-Daily Fluticason Furoate in the Treatment of Asthma, dated Feb. 4, 2009.
Bleeker, et al. "Consistently favorable safety profile of Fluticasone Furoate (FF), a once-daily (od) inhaled corticosteroid (ICS), across a range of treatment steps in patients with uncontrolled asthma", American Thoracic Society International Conference Abstracts: C31 Optimizing therapeutic strategies in airways disease, thematic poster session, May 15, 2011.
Bossert, et al., "Effect of Mixing on the Lubrication of Crystalline Lactose by Magnesium Stearate" 1980; Drug Development and Industrial Pharmacy; vol. 6(6); pp. 573-589.
BREO ELLIPTA Prescribing Information. May 2017. pp. 1-58.
Busse, et al., "Expert Panel Report 3 (EPR-3): Guidelines for the Diagnosis and Managment of Asthma—Summary Report 2007" Allergy, Asthma & Immunology; 2007; pp. S94- S138; vol. 120, No. 5.
Busse, et al., "Fluticasone Furoate (FF), A Once-Daily Inhaled Corticosteroid (ICS). In efficacious in patients with uncontrolled asthma across a range of treatment steps", American Thoracic Society International Conference Abstracts: C31 Optimizing therapeutic strategies in airways disease, thematic poster session, May 15, 2011.
Caverly et al., "Fluticasone furoate, vilanterol and lung function decline in patients with moderate COPD and heightened cardiovascular risk", AJRCCM, 2018; pp. 47; vol. 197.
Cazzola, et al., "Beta2-adrenoceptor agonists: current and future direction" British Journal of Pharmacology; 2011, vol. 163; pp. 4-17.
Cazzola, M. et al., "The scientific rationale for combining long-acting beta2-agonists and muscarinic antagonists in COPD", Pulmonary Pharmacology & Therapeutics, Academic Press, GB, vol. 23, No. 4, Aug. 1, 2010, pp. 257-267.
Clinical Trial History of Changes for Study NCT00766090, Oct. 2, 2008.
Clinical Trial Protocol for Clinical Trial with Identifier NCT00606684, Jan. 21, 2020.
Committee for medicinal products for human use: Guideline on the pharmaceutical quality of inhalation and nasal products, London, Jun. 21, 2006.
Communication of Notice of Opposition for EP Application No. 11755043.4 (Teva UK Ltd.) dated Apr. 1, 2016.
Communication of Notice of Opposition for EP Application No. 11755043.4 (Oser Andreas) dated Mar. 31, 2016.
Communication of Notice of Opposition for EP Application No. 11755043.4 (Generics UK Limited) dated Mar. 31, 2016.
Covelli et al., "Efficacy and safety of fluticasone furoate/vilanterol or tiotropium in subjects with COPD at cardiovascular risk", International Journal of COPD, (2016): 11, pp. 1-12.
Decision T 0007/07; Jul. 7, 2011.
Decision T 0239/16; Sep. 13, 2017.
Declaration of Helsinki; Oct. 2008.
Dehns Opposition to European patent No. 2400950 to Glaxo Group Limited dated Feb. 18, 2020.
Donohue et al., A randomized, double-blind dose-ranging study of the novel Lama GSK573719 in patients with COPD. Respir Med. Jul. 2012;106(7):970-9.
Donohue, et al., Efficacy and safety of once-daily umeclidinium/vilanterol 62.5/25 mcg in COPD. Respir Med. Oct. 2013; 107(1), pp. 1538-1546.
Donohue et al., Magnitude of umeclidinium/vilanterol lung function effect depends on monotherapy responses: Results from two randomised controlled trials. Respir Med. Mar. 2016;112:65-74.
Donohue et al., "Minimal Clinically Important Differences in COPD Lung Function." COPD: Journal of Chronic Obstructive Pulmonary Disease; 2005; pp. 111-124; vol. 2.

Dransfield et al., "Once-daily inhaled fluticasone furoate and vilanterol versus vilanterol only for prevention ofexacerbations of COPD: two replicate double-blind, parallel-group, randomized controlled trials", www.thelancet.com/respiratory, vol. 1, May 2013, pp. 210-223.
Dransfield, et al. "Efficacy and safety of once-daily fluticasone furoate/vilanterol (100/25 mcg) versus twice-daily uticasone propionate/salmeterol (250/50 mcg) in COPD patients" Respiratory Medicine; 2014; pp. 1171-1179; vol. 108.
EKLIRA™ GENUAIR™ 322 micrograms inhalation powder—Summary of Product Characteristics.
El-Gendy et al., "Development of Budesonide NanoCluster Dry Powder Aerosols: Formulation and Stability." Journal of Pharmaceutical Sciences, vol. 101, No. 9 (Sep. 2012) pp. 3445-3455.
Experimental data on relative humidity (patentee's submission of 19.02.2018, cited in opposition of EP2611423).
Relvar Ellipta device (patentee's submission of 19.02.2018, cited in opposition of EP2611423).
Regulatory Dossier for Relvar Ellipta, pp. 1-6, cited in opposition of EP2611423, Feb. 19, 2018.
Annex, Submission dated Apr. 24, 2015 in the European patent application No. 11 755 042.6 filed by the same Applicant, cited in opposition of EP2611423.
T 0805/93 (OP3's submission of Jan. 18, 2018), opposition of EP2611423.
World Health Organization, WHO Technical Report Series, No. 953, 2009, Annex 2: Stability testing of active pharmaceutical ingredients and finished pharmaceutical products.
Physician's Desk Reference, Thompson Reuters, 63rd edition, 2009, pp. 1276-1288, 1435-1440 and 1594-1601.
Relvar Ellipta Package Leaflet; Jan. 2, 2019; pp. 1-12.
U.S. Appl. No. 12/353,436, filed Jan. 14, 2009, Muscarinic Acetylcholine Receptor Antagonists.
US Office Action for U.S. Appl. No. 13/510,962, dated Jan. 14, 2015.
US Office Action for U.S. Appl. No. 13/510,962, dated Jun. 10, 2013.
US Office Action for U.S. Appl. No. 13/510,962, dated Jun. 16, 2015.
US Office Action for U.S. Appl. No. 13/510,962, dated Jun. 20, 2014.
US Office Action for U.S. Appl. No. 13/510,962, dated Oct. 9, 2013.
Response filed Apr. 14, 2015 to US Office Action for U.S. Appl. No. 13/510,962, dated Jan. 14, 2015.
Response filed Aug. 20, 2014 to US Office Action for U.S. Appl. No. 13/510,962, dated Jun. 20, 2014.
Response filed Jun. 21, 2013 to US Office Action for U.S. Appl. No. 13/510,962, dated Jun. 10, 2013.
U.S. Appl. No. 13/510,962, filed Aug. 20, 2012, Combinations of A Muscarinic Receptor Antagonist and A Beta-2 Adrenoreceptor Agonist.
U.S. Appl. No. 13/401,890, filed Feb. 22, 2012, Muscarinic Acetylcholine Receptor Antagonists.
U.S. Appl. No. 13/819,149, Request for Continued Examination filed Nov. 23, 2015.
U.S. Appl. No. 13/819,149, Final Office Action mailed Aug. 27, 2015.
U.S. Appl. No. 13/819,149, Applicant's response to Office Action of Mar. 6, 2015, dated Jun. 3, 2015.
U.S. Appl. No. 13/819,149, Non-final Office Action, mailed Mar. 6, 2015.
U.S. Appl. No. 13/819,149, Request for Continued Examination filed Sep. 17, 2014.
U.S. Appl. No. 13/819,149, Non-Final Rejection, mailed Jun. 27, 2019.
U.S. Appl. No. 13/819,149, Claims and Applicants Arguments/Remarks Made in Amendment, filed Apr. 5, 2019.
U.S. Appl. No. 13/819,149, filed Feb. 26, 2013.
U.S. Appl. No. 13/819,149, Applicants' Amendment and Claims, dated Feb. 22, 2017.
U.S. Appl. No. 13/819,149, Final Rejection, dated Oct. 3, 2016.
U.S. Appl. No. 13/819,149, Restriction Requirement mailed Sep. 26, 2013.

(56) References Cited

OTHER PUBLICATIONS

U.S. Appl. No. 13/819,149, Response to Restriction Requirement filed Oct. 21, 2013.
U.S. Appl. No. 13/819,149, Non-Final Rejection Mailed Dec. 5, 2013.
U.S. Appl. No. 13/819,149, Final Office Action dated Jun. 20, 2014.
U.S. Appl. No. 13/819,184, filed Feb. 26, 2013.
U.S. Appl. No. 13/819,184, "Applicant's Response to Non-Final Rejection of Oct. 2, 2017", dated Dec. 11, 2017.
U.S. Appl. No. 13/819,184, "Non-Final Rejection" dated Apr. 16, 2018.
U.S. Appl. No. 13/819,184, "Non-Final Rejection" dated Oct. 2, 2017.
U.S. Appl. No. 13/819,184, Non-Final Office Action dated Sep. 24, 2013.
U.S. Appl. No. 13/819,184, Response to Office Action filed Dec. 17, 2013.
U.S. Appl. No. 13/819,184, Non-Final Rejection mailed May 1, 2014.
U.S. Appl. No. 13/819,184, Response to Non-Final Rejection filed Jul. 17, 2014.
U.S. Appl. No. 13/819,184, Amendment filed dated Feb. 3, 2015.
Shur, J., et al., "From single excipients to dual excipient platforms in dry powder inhaler products." Intl' Journal of Pharmaceutics; 2016; pp. 374; vol. 514.
Siler et al., "A randomized, phase III trial of once-daily fluticasone furoate/vilanterol 100/25 mcg versus once-daily vilanterol 25 mcg to evaluate the contribution on lung function of fluticasone furoate in the combination in patients with COPD", Respiratory Medicine, 123, (2017), pp. 8-17.
Staniforth, et al., "Interparticle forces in binary and ternary ordered powder mixes." J_ Pharm. Pharmacol.; 1982; pp. 141-145; vol. 34.
Sterling, et al., "Dose-Related Efficacy and Optimal Once-Daily (od) Dosing Interval of the Long-Acting Beta2 Agonist(laba), Vilanterol Trifenatate (vi), In Adults With Persistent Asthma" Am J Respir Crit Care Med, May 17, 2011; C39 Novel Therapeutic Options in Airways Disease; Thematic Poster Session.
Submissions of the Proprietor in the examination proceedings related to the opposed Eur. Pat. Appl. 09 779 096.8-1219 dated Feb. 4, 2013; Response to Aug. 9, 2012 Communication.
Telko, et al., "Dry Powder Inhaler Formulation" Respiratory Care; 2005; vol. 50, No. 9; pp. 1209-1227.
The London Gazette, "Medicines Control Agency—Licenses Granted." Feb. 23, 2001; [https://www.thegazette.co.uk/notice/L-5613-1003].
Theravance Press Release dated Apr. 2, 2007.
To, Masako, et al., "Fluticasone Furoate, A Novel Enhanced-affinity Inhaled Corticosteroid (ICS), Has More Potent Anti-inflammatory Effects Than Fluticasone Propionate in Peripheral Blood Mononuclear Cells From Asthma and COPD Patients", Am J RespirCrit Care Med; 2010; vol. 181.
Vaczek, "Dialing in stable packaging for sensitive drugs" Pharmaceutical and Medical Packaging News; 2010.
Van Kamp, et al., "The Role of Water Uptake on Tablet Disintegration" 1986; Pharm Acta Helv; vol. 61 (1); pp. 22-29.
Vestbo, et al., "Effectiveness of Fluticasone Furoate—Vilanterol for COPD in Clinical Practice" The New England Journal of Medicine; 2016; pp. 1253-1260; vol. 375.
Vestbo et al., "Fluticasone furoate and vilanterol and survival in chronic obstructive pulmonary disease with heightened cardiovascular risk (SUMMIT): a double-blind randomize controlled trial" www.thelancet.com, vol. 387, Apr. 30, 2016, pp. 1817-1826.
Wade, A, et al., "Handbook of Pharmaceutical Excipients 2nd Edition" 1994; pp. 252-261; London: The Pharmaceutical Press.
Welte, T. et al., "Efficacy and Tolerability of Budesonide/Formoterol Added to Tiotropium in Patients with Chronic Obstructive Pulmonary Disease" Amer. J. Resp. & Critical Care Med. vol. 180, pp. 741-750 (2009).
Westmeier et al., "Combination Particles Containing Salmeterol Xinafoate and Fluticasone Propionate: Formulation and Aerodynamic Assessment," Journal of Pharmaceutical Sciences, vol. 97, No. 6, Jun. 2008.
Wetterlim; "Turbuhaler: A New Powder Inhaler for Administration of Drugs to the Airways"; Pharm. Res.; 1988; vol. 5 (8); pp. 506-508.
Williams, R.O., III, et al., "Investigation of moisture scavengers in pressurized metered-dose inhalers," 2000:S.T.P. Pharma Sciences; vol. 10(3); pp. 243-250 (Abstract).
Woodcock, et al., "Efficacy and Safety of Fluticason FuroateNilanterol Compared With Fluticasone Propionate/Salmeterol Combination in Adult and Adolescent Patients with Persistent Asthma" Chest; 2013; pp. 1222-1229; vol. 144, No. 4.
World Health Organization, The top 10 causes of death. WHO Fact Sheet No. 310, retrieved online at: http://www.who.hl/mediacentre/factsheets/fs310/en/, Updated May 2014.
Young, et al., "Influence of Humidity on the Electrostatic Charge and Aerosol Performance of Dry Powder Inhaler Barrier Based Systems." Pharmaceutical Research; May 2007; vol. 24, No. 5; pp. 963-970.
Zeng, "Particle Interactions in dry powder formulations for inhalation", Department of Pharmacy; King's College London: Chapter 5: pp. 131-173.
EP1232745 Statement of Grounds of Appeal dated Mar. 25, 2010.
EP1232745 Decision of the Enlarged Board of Appeal in review procedure dated Jul. 30, 2012.
EP1232745 Written Decision in Preparation to/during Oral Proceedings dated Aug. 27, 2009, pp. 1-34.
EP1232745 Reply of the Patent Proprieter to the Notice(s) of Oppositions dated Oct. 9, 2008.
EP1232745 Reply of the Patent Proprieter to the Notice(s) of Oppositions dated Sep. 25, 2008.
EP1232745 Notice of Opposition dated Dec. 6, 2007.
EP1232745 Notice of Opposition dated Dec. 10, 2007.
EP1232745, Minutes of the Oral Proceedings {Opposition division}, Oct. 27, 2009, pp. 1-10.
EP1232745, F3032 Notification of the Decision, pp. 1-23, May 18, 2011.
EP2283817, Notice of Opposition dated Feb. 16, 2017, pp. 1-21.
EP2283817, Reply of the Patent Proprieter to the Notice(s) of Opposition dated Aug. 10, 2017.
EP2283817, "Brief Communication—Opposition Proceedings, Jul. 14, 2017, pp. 1-6".
EP2283817, Brief Communication—Oral Proceedings, Aug. 28, 2018, pp. 1-164.
EP2283817, "Written Submission in Preparation to/during Oral Procedure" Aug. 23, 2018, pp. 1-31.
View of NCT01128569 on Jun. 4, 2010, ClinicalTrials.gov archive [online], Jun. 4, 2010, [search at Apr. 30, 2014], URL, <http://clinicaltrials_gov/archive/NCT01128569/2010_06_04>.
ClinicalTrials Identifier: NCT01128569 "A Randomised, Doubleblind, Placebo-controlled, Three-way Crossover, Repeat Dose Pilot Study Comparing the Effect of Inhaled Fluticasone Furoate/GW642444M Combination and Fluticasone Furoate on the Allergen-induced Early Asthmatic Response in Subjects With Mild Asthma"; ClinicalTrials.gov archive: First received May 20, 2010; Last updated May 29, 2014.
View of NCT01134042 on Jul. 16, 2010, ClinicalTrials.gov archive [online], Jul. 16, 2010. [search at Apr. 30, 2014], URL, <http://clinicaltrials.gov/archive/NCT01134042/2010_07_16>.
ClinicalTrials Identifier: NCT01134042 "HZA106829: A Randomised, Double-blind, Parallel Group, Multicentre Study of Fluticasone Furoate/GW642444 Inhalation Powder, Fluticasone Furoate Inhalation Powder Alone, and Fluticasone Propionate Alone in the Treatment of Persistent Asthma in Adults and Adolescents" ClinicalTrials.gov archive: First received May 27, 2010; Last updated Jun. 6, 2013.
Reply of the Patent Proprietor to the Notice of Opposition for EP2611423, Dec. 6, 2016, pp. 1-50.
Reply of the Patent Proprietor to the Notice of Opposition for EP2611423, Dec. 6, 2016, pp. 1-49.

(56) References Cited

OTHER PUBLICATIONS

Patent Proprietor's Reply to Appeal, EP2611423, Feb. 4, 2019, pp. 1-18.
Patent Proprietor's Reply to Appeal, EP2611423, Feb. 6, 2019, pp. 1-18.
Statement of Grounds of Appeal, EP2611423, Sep. 27, 2018, Dr. Andreas Oser, pp. 1-25.
Statement of Grounds of Appeal, EP2611423, Sep. 27, 2018, Generics UK, pp. 1-15.
Statement of Grounds of Appeal, EP2611423, Sep. 26, 2018, Teva, pp. 1-15.
Written Submission in preparation to/during oral proceedings, EP2611423, Jan. 8, 2018, Teva, pp. 1-15.
Written Submission in preparation to/during oral proceedings, EP2611423, Jan. 8, 2018, Dr. Andreas Oser, pp. 1-12.
Grounds for the Decision (Annex)—Opposition, EP2611423, May 17, 2018, pp. 1-17.
OPP D40—X. M. Zeng et al Particle interactions in dry powder formulations for inhalation, Taylor & Francis, London and New York, 20301, Chapter 5, pp. 144-157.
OPP D41—www.clinicaltrial.gov; Identifier NCT00519376 dated Oct. 9, 2008 "A Randomised, Singledose, Dose Ascending, Double-blind, Placebo Controlled, Four-way, Incomplete Block Crossover Study to Investigate the Safety, Tolerability, Pharmacokinetics and Pharmacodynamics of Inhaled Doses of GW642444M With Magnesium Stearate in COPD Patients" Available from: https://clinicaltrials.gov/ct2/history/NCT00519376?V_3= View#Study Page Top.
OPP D42—www.clinicaltrial.gov; Identifier NCT00606684 dated Nov. 6, 2008 "Study B2C111045, A Dose-Finding Study of GW642444 Versus Placebo in Patients With COPD" Available from: https://clinicaltrials.gov/ct2/history/NCT00606684?V_11=View#StudyPage Top.
OPP D44—S Newham Evolution of dry powder inhaler design, formulation, and performance, Res Med., v96,2002,293-294.
OPP D45—H. Chrystyn, "The DiskusTM: a review of its position among dry powder inhaler devices", International Journal of Clinical Practice, 61, 6, 1022-1036, Jun. 2007.
OPP D46—S. Newman "How Well Do in Vitro Particle Size Measurements Predict Drug Delivery In Vivo?" Journal of Aerosol Medicine 1998, 11, S97-S104.
OPP D47—T. Peng, S. Lin, B. Niu, X. Wang, Y. Huang, X. Zhang, G. Li, X. Pan and C. Wu ,,Influence of physical properties of carrier on the performance of dry powder inhalers Acta Pharmaceutica Sinica B 2016, 6, 308-318.
OPP D48—N. Islam, P. Stewart, I. Larson and P. Hartley ,, Effect of Carrier Size on the Dispersion of Salmeterol Xinafoate from Interactive Mixtures Journal of Pharmaceutical Sciences Apr. 2004, 93, 1030-1038.
OPP D49—V. N. P. Le, T. H. Hoang hi, E. Robins and M. P. Flament, AAPS PharmSciTech Jun. 2012, 13, 477-484.
OPP D50—B. Mei Jin Tanm L. Wah Chan and p. Wan Sia Heng, ,,Chapter 11 Milling and Blending: Producing the Right Particles and Blend Characeristics for Dry Powder Inhalation Pharmaceutical Inhalation Aerosol Technology Third Edition 2019, p. 273-284.
OPP D51—J. Shur, H. Harris, M. D. Jones, J. S. Kaerger and R. Price ,, The Role of Fines in the Modification of the Fluidization and Dispersion Mechanism Within Dry Powder Inhaler Formulations Pharmaceutical Research Jul. 2008, 25, 1931-1940.
OPP D52—M. J. Telko and A. J. Hickey "Dry Powder Inhaler Formulation" Respiratory Care Sep. 2005, 50, 1209-1227.
OPP D53—S. J. Charlton "Agonist efficacy and receptor desensitization: from partial truths to a fuller picture" British Journal of Pharmacoloy 2009, 158, 165-168.
OPP D55—print-out from https://clinicaltrials.gov/ct2/show/NCT01147848, version dated Jan. 18, 2017.
OPP D56—print-out from https://clinicaltrials.gov/ct2/show/NCT00606684, version dated Feb. 1, 2008.
OPP D57—print-out from https://clinicaltrials.gov/ct2/show/NCT00606684, version dated Dec. 16, 2016.
OPP D58—print-out from https://www.gsk-studyregister.com/study?uniqueStudyId=B2C111045, Mar. 9, 2020.
OPP D59—print-out from https://clinicaltrials.gov/ct2/show/NCT00600171, version dated Jan. 22, 2009.
OPP D60—print-out from https://clinicaltrials.gov/ct2/show/NCT00600171, version dated Dec. 16, 2016.
OPP D61—print-out from https://www.gsk-studyregister.com/study?uniqueStudyId=B2C109575, Mar. 9, 2020.
OPP D62—print-out from https://clinicaltrials.gov/ct2/show/NCT00731822, version dated Aug. 8, 2008.
OPP D63—print-out from https://clinicaltrials.gov/ct2/show/NCT00731822, version dated Dec. 8, 2016.
OPP D64—print-out from https://www.gsk-studyregister.com/study?uniqueStudyId=HZC111348, Mar. 9, 2020.
OPP D65—print out from https://pipelinereview.com/index.php/2008122224291/Small-Molecules/GS Kand-Theravance-an nou nce-positive-phase-2b-results-for-LABA-444-in-the-treatment-of-COPD-in-the-Horizon-Development-Programme.html, press release dated Dec. 22, 2008.
OPP D66—print out from http://investor.i nva.com/news-releases/news-release-details/th eravance- reportsfourth-quarter-and-full-year-2008-results, press release dated Feb. 12, 2009.
OPP D67—B. Beilmann, R. Kubiak, P. Grab, H. Hausler and P. Langguth 11Effect of Interactive Ternary Mixtures on Dispersion Characteristics of Ipratropium Bromide in Dry Powder Inhaler Formulations AAPS PharmSciTech 2007 Apr. 20, 2007, 8, E1-E8.
OPP D68—S. Lawrence Lee, W. P. Adams, B. V. Li, D. P. Connr, B. A. Chowdhury and L. X. Yu ,,In Vitro Considerations to Support Bioequivalence of Locally Acting Drugs in Dry Powder Inhalers for Lung Diseases The AAps Journal Sep. 3, 2009, 11, 414-423.
OPP D71—print out from https://www.ema.europa.eu/en/documents/scientific-guideline/note- guidanceclinical-investigation-medicinal-products-treatment-asthma_en.pdf, press release from Nov. 21, 2002.
OPP D72—print out from Belgian medicinal product register 2008 (Repertoire Commente Des Medicaments 2008).
OPP D75—Global Initiative for Chronic Obstructive Lung Disease (GOLD), "Global Strategy for the diagnosis, management, and prevention of chronic obstructive pulmonary disease" 2006, MCR Vision, Inc.
OPP D76—Global Initiative for Asthma (GINA), "Global Strategy for Asthma Management and Prevention" 2008 (update).
OPP D77—M. Cazzola et al., Ultra long-acting j32-agonists in development for asthma and chronic obstructive pulmonary disease, Expert Opin. Investig. Drugs (2005) 14(7), pp. 775-783.
OPP D79—M. G. Matera et al., Ultra-long-acting j32-adrenoceptor agonists—an emerging therapeutic option for asthma and COPD?, Drugs 2007; 67(4), pp. 503-515.
OPP D82—USAN information vilanterol and vilanterol trifenatate (downloaded on Feb. 13, 2020).
OPP D83—USAN information fluticasone furoate (downloaded on Feb. 13, 2020).
OPP D84—R. Kempsford et al.; The pharmacodynamics, pharmacokinetics and tolerability of repeat doses of the novel inhaled long-acting beta2 adrenoceptor agonist (LABA) GW642444 (25, 50 and 100 mcg) in healthy subjects; Am J Respir Crit Care Med 181; 2010:A4461.
OPP D86—US Pharmacopeia, USP 31 Vol. 1, pp. 605-607 as in force of May 1, 2008.
OPP D87—Drugs for the treatment of respiratory diseases, edited by D. Spina et al.; Cambridge University Press 2003.
OPP D88—Definition of the term "respiratory disease" downloaded on Feb. 12, 2020 from the online NCI Dictionary of Cancer Terms https://www.cancer.gov/publications/dictionaries/cancerterms/def/respiratory-disease.
Opposition Submission to EP2400950 by HGF filed Feb. 21, 2020.
Opposition Statement EP2400950 by Teva filed Feb. 22, 2020.
Opposition Statement EP2400950 by NLO filed Feb. 21, 2020.
Opposition Statement EP2400950 by Sandoz filed Feb. 24, 2020.
PUBCHEM: "Vilanterol-C24H33CI2NO5," Database Pubchem Compound, Database Accession No. CID 10184665, National Center for Biotechnology Information, Oct. 25, 2006, XP055943094, Retrieved from URL: https://pubchem.ncbi.nlm.nih.gov/compound/10184665.

(56) References Cited

OTHER PUBLICATIONS

Rabe K.F., et al., "Global Strategy for the Diagnosis, Management, and Prevention of Chronic Obstructive Pulmonary Disease,"American Journal of Respiratory and Critical Care Medicine, 2007, vol. 176 (6), pp. 532-555.
Request for Continued Examination for U.S. Appl. No. 14/970,945, dated Apr. 11, 2017, 9 Pages.
Request for Continued Examination for U.S. Appl. No. 14/970,945, dated Nov. 23, 2016, 1 Page.
Requirement for Restriction for U.S. Appl. No. 15/678,246, dated Dec. 1, 2017, 8 Pages.
Requirement for Restriction/Election for U.S. Appl. No. 14/651,988, dated Feb. 25, 2016, 8 Pages.
Response filed on Jul. 6, 2017, to Non Final Office Action mailed Apr. 7, 2017 for U.S Appl. No. 13/819,149, 07 Pages.
Response filed on Jul. 10, 2016, to Non Final Office Action mailed Feb. 12, 2016 for U.S. Appl. No. 14/970,945, 19 Pages.
Response filed on Jun. 10, 2016, to Non Final Office Action mailed Feb. 12, 2016 for U.S. Appl. No. 14/970,945, 25 Pages.
Response filed on Mar. 10, 2014, to Non Final Office Action mailed Oct. 9, 2013 for U.S. Appl. No. 13/510,962, 10 Pages.
Response filed on Jun. 12, 2015, to Office Action mailed Apr. 15, 2016 for U.S. Appl. No. 14/651,988, Combination of Umeclidinium, Fluticasone Propionate and Salmeterol Xinafoate for Use in the Treatment of Inflammatory or Respiratory Tract Diseases, 9 Pages.
Response filed on May 2, 2016, to Office Action dated Feb. 2, 2016 for U.S. Appl. No. 14/124,276, 9 Pages.
Response filed on Oct. 21, 2013, to Office Action mailed Sep. 26, 2013 for U.S. Appl. No. 13/819,149, 5 Pages.
Response filed on Oct. 22, 2013. to Office Action dated Aug. 12, 2013 for Australian Patent Application No. 2011298409, Applicant's Response to Examination Report, 13 Pages.
Response filed on Sep. 23, 2016, to Non Final Office Action mailed Jun. 23, 2016 for U.S. Appl. No. 14/651,988, 10 Pages.
Response filed on Oct. 24, 2016, to Final Office Action mailed Aug. 24, 2016 for U.S. Appl. No. 14/970,945, 7 Pages.
Response filed on Feb. 26, 2014, to Non Final Office Action mailed Dec. 5, 2013 for U.S. Appl. No. 13/819,149, 06 Pages.
Response filed on Sep. 26, 2018, to Non Final Office Action mailed Aug. 27, 2018 for U.S. Appl. No. 13/819,149, 05 Pages.
Response filed on Jun. 28, 2016, to Non Final Office Action mailed Mar. 30, 2016 for U.S. Appl. No. 13/819,149, 07 Pages.
Response to Restriction for U.S. Appl. No. 15/678,246, mailed Feb. 1, 2018, 9 Pages.
Response to the Oppositions for European Patent No. 2506844, dated Apr. 29, 2019, 44 Pages.
Response to the Submission filed by Opponent 1 on Jun. 17, 2019 for European Patent No. 2506844, dated Sep. 6, 2019, 16 Pages.
Royal Courts of Justice: "*Actavis Ors v ICOS & Anr*," Neutral Citation Number: [2017] EWCA Civ 1671, Nov. 1, 2017, 45 Pages, OPP D36.
Rule 116 EPC submission for Opposition of EP Application No. 10781527.6 by Dr. Markus Breuer (Oppo 02), dated Jul. 22, 2020, 24 Pages.
Rule 116 EPC submission for Opposition of EP Application No. 10781527.6 by Sima Patent Lisanslama Hizetleri Ltd STI (Oppo 03), dated Jul. 13, 2020, 12 Pages.
Rule 116 EPC submission for Opposition of EP Application No. 10781527.6 by Teva UK Limited (Oppo 01), dated Jul. 23, 2020, 19 Pages.
Schmidt R., "Dose-Finding Studies in Clinical Drug Development," European Journal of Clinical Pharmacology, 1998, vol. 34, pp. 16-19.
Spiriva HandiHaler (tiotropium) Label, 2009 , 29 Pages.
Statement of Mr Gary Muirhead for European Publication No. EP2400950, dated Feb. 18, 2020, 7 Pages, OPP D39.
Statement of Opposition for European Patent No. 2506844, Teva UK Limited, filed Sep. 17, 2018, 17 Pages.

Sterling R., et al., "Efficacy and Optimal Dosing Interval of the Long-acting Beta2 Agonist, Vilanterol, in Persistent Asthma: A Randomised Trial," Respiratory Medicine, 2012, vol. 106, pp. 1110-1115.
Study Report Relating to Clinical Study NCT00976144, Mar. 2010, pp. 1-53, Retrieved from URL: http://www.gsk-studyregiester.com/en/.
Submission of GGL in Examination of European Patent Application No. 09779096.8-1219, Which Issued as Opposed Patent EP2400950,Opp-1, D1, dated Feb. 4, 2013, 2 Pages.
Submissions of the Proprietor in the Examination Proceedings Related to the Opposed European Patent Application No. 09779096.8-1219 dated Feb. 4, 2013, pp. 1-2, Response to Aug. 9, 2012 Communication.
Tal Singer R., et al., "Initial Assessment of Single and Repeat Doses of Inhaled Umeclidiniumin Patients with Chronic Obstructive Pulmonary Disease: Two Randomised Studies," European Journal of Pharmacology, 2013, vol. 701, pp. 40-48.
The Supreme Court Judgment: "*Actavis Group Ptc Ehf and Others (Respondents) V Icos Corporation and Another (Appellants)*," Mar. 27, 2019, pp. 1-38, (39 Pages).
Villetti G., et al., "Bronchodilator Activity of (3R)-3-III(3-fluorophenyl) {3,4,5-trifluorophenyl)methyl]amino] carbonyl] oxy]-1-[2-oxo-2-(2-thienyl)ethyl]-1-azoniabicyclo[2.2.2] Octane Bromide (CHF5407), A Potent, Long-Acting, and Selective Muscarinic M3 Receptor Antagonist," The Journal of Pharmacology and Experimental Therapeutics, 2010, vol. 335, No. 3, pp. 622-635.
Waldeck B., "Some Pharmacodynamic Aspects on Long-acting Beta-adrenoceptor Agonists, "General Pharmacology, 1996, vol. 27(4), pp. 575-580.
Wanzhen Y., "Study on the Changes of Airway Muscarinic M Receptors and Anticholinergic Therapy in Chronic Obstructive Pulmonary Disease" Chinese Journal of Tuberculosis and Respiratory Diseases, 2005, vol. 28 (7), pp. 484-487.
Warng Perng D., et al., "Additive Benefits of Tiotropium in COPD Patients Treated With Long-acting Beta Agonists and Corticosteroids, "Respirology (Carlton, Vic.), 2006, vol. 11(5), pp. 598-602.
"WHO Drug Information," Geneva, 2008, vol. 22, No. 2, p. 132. 2 Pages.
Extended European Search Report for European Application No. 17206132.7, mailed May 24, 2018, 16 Pages.
FDA Approved Drug Products, Press Release for Anoro US Approval, 2019, pp. 3.
FDA: "FDA Approves Anoro Ellipta To Treat Chronic Obstructive Pulmonary Disease," Gov Details of Anoro Ellipta, Approved on Dec. 18, 2013, 3 Pages,.
File History for U.S. Appl. No. 14/970,945, filed Dec. 16, 2015, 382 Pages.
Final Office Action for U.S. Appl. No. 13/819,149, mailed Jan. 7, 2019, 14 Pages.
Final Office Action for U.S. Appl. No. 13/819,149, mailed Oct. 25, 2017, 13 Pages,.
Final Office Action for U.S. Appl. No. 14/124,276, mailed Jul. 6, 2016, 22 Pages.
Final Office Action for U.S. Appl. No. 14/970,945, mailed Aug. 24, 2016, 54 Pages.
Glaxosmithkline: "GSK & Theravance announce positive phase-2b results of COPD trial," OPP-D65, Dec. 24, 2008, 3 Pages.
Glaxosmithkline: "GSK and Theravance Announce Positive Phase 2b Results for LABA 444 in the Treatment ofCOPD in the Horizon Development Programme," OPP-D65, Dec. 22, 2008, 2 Pages, [Retrieved on Feb. 19, 2020] Retrieved from URL: https://pipelinereview.com/index.php/2008122224291/Small-Molecules/GSKand-Theravance-announce-positive-phase-2b-results-for-LABA-444-in-the-treatment-of-COPD-in-the-Horizon-Development-Programme.html.
Gold Teams: "The Global Strategy for the Diagnosis, Management, and Prevention of Chronic Obstructive Pulmonary Disease," Executive Summary. Global Initiative for Chronic Obstructive Lung Disease, 2009, 44 Pages, XP055520517.
Gross N. J., "Anticholinergic Agents in Asthma and COPD," European Journal of Pharmacology, Elsevier Science, NL, Mar. 8,

(56) References Cited

OTHER PUBLICATIONS 2006, vol. 533, No. 1-3, pp. 36-39, XP028028951, ISSN: 0014-2999, DOI: 10.1016/j.ejphar.2005.12.072.
GSK: "GSK Filing Accepted by European Medicines Agency for Trelegy Ellipta Use in Adult Patients with Asthma," Press Release, Feb. 27, 2020, 4 Pages.
Gupta A., et al., "Difference in the Lubrication Efficiency of Bovine and Vegetable-Derived Magnesium Stearate During Tabletting," American Association of Pharmaceutical Scientists PharmSciTech, Jun. 2, 2009, vol. 10, No. 2, pp. 500-504, XP055943118, DOI: 10.1208/s12249-009-9229-y.
Haiyan Z., "Research Progress of Anti-Asthma Drugs 2 Receptor Agonists," Chinese Journal of Medicinal Chemistry.
ICH-E4 FDA: "Guideline for Industry Dose Response Information to Support Drug Registration," Federal Register, OPP D34, ICH-E4 FDA, Nov. 9, 1994, vol. 59, No. 216, pp. 1-15, (17 Pages), Retrieved from URL: https://www.fda.gov/regulatory-information/search-fdaguidance-documents.
International Preliminary Report on Patentability for International Application No. PCT/EP2010/068429, mailed Jun. 14, 2012. 9 Pages.
International Search Report and Written Opinion for International Application No. PCT/EP2010/068429, mailed Mar. 11, 2011, 12 Pages,.
Jr. Allen L.V., et al., "Ansel's Pharmaceutical Dosage Forms and Drug Delivery Systems," Lippincott Williams & Wilkins, 2005, Chapters 2 and 6, pp. 26-66, (44 Pages), OPP D32.
Kempsford R., et al., "GW642444, A Novel Inhaled Long-acting Beta2 Adrenoceptor Agonist (LABA), At Single Doses of 25, 50 and 100 mcg, Is Well Tolerated And Demonstrates Prolonged Bronchodilation in COPD Patients," American Journal of Respiratory and Critical Care Medicine, 2010, vol. 181, A4447, 1 Page.
Kuna P., et al., "Once-daily Dosing with Budesonide/Formoterol Compared with Twice-Daily Budesonide/Formoterol and Once-daily Budesonide in Adults with Mild to Moderate Asthma," Respiratory Medicine, 2006, vol. 100, pp. 2151-2159.
Laine D.L., et al., "Design, Synthesis, and Structure—Activity Relationship of Tropane Muscarinic Acetylcholine Receptor Antagonists," Journal of Medicinal Chemistry, 2009, vol. 52, pp. 5241-5252.
Letter of the USAN Relating to Umeclidinium Bromide dated May 25, 2011, 2 Pages.
Letter of the USAN Relating to Umeclidinium dated May 25, 2011, 2 Pages.
Letter of the USAN Relating to Vilanterol dated Sep. 30, 2009, 3 Pages,.
Letter of the USAN Relating to Vilanterol Trifenatate dated Sep. 30, 2009, 3 Pages.
List of Data for the Decision For European Appeal No. T 1753/06 3.3.01, dated May 6, 2009, 75 Pages, OPP D38.
Lotvall J., et al., "24-h Duration of the Novel LABA Violanterol Trifenatale in Asthma Patients Treated with Inhaled Corticosteroids," European Respiratory Journal, 2012, vol. 40, pp. 570-579,.
Lotvall J., "Pharmacological Similarities and Differences Between Beta2-Agonists, "Respiratory Medicine, 2001, vol. 95, pp. S7-S11.
Maleki-Yazdi M.R., et al., "Efficacy and Safety of Umeclidinium/vilanterol 62.5/25 Mcg and Tiotropium 18 Mcg in Chronic Obstructive Pulmonary Disease: Results of a 24-week, Randomized, Controlled Trial, "Respiratory Medicine, 2014, vol. 108(12), pp. 1752-1760.
Muirhead G.J., "Curriculum Vitae," Curriculum Vitae of Mr Gary Muirhead, pp. 1-9, OPP D39A.
Navarrete B.A., et al., "Umeclidinium/vilanterol Versus Tiotropium/olodaterol in Maintenance-naive Patients With Moderate Symptomatic Chronic Obstructive Pulmonary Disease: a Post Hoc Analysis, "Pulmonary Therapy, 2018, vol. 4(2), pp. 171-183.
Nials A. T., et al., "Effects of Beta-adrenoceptor Agonists in Human Bronchial Smooth Muscle, "British Journal of Pharmacology, 1993, vol. 110(3), pp. 1112-1116.

Non-Final Office Action for U.S. Appl. No. 13/819,149, mailed Apr. 7, 2017. 19 Pages.
Non-Final Office Action for U.S. Appl. No. 13/819,149, mailed Aug. 27, 2018, 14 Pages.
Non-Final Office Action for U.S. Appl. No. 13/819,149, mailed Mar. 30, 2016, 19 Pages.
Non-Final Office Action for U.S. Appl. No. 14/124,276, mailed Feb. 2, 2016, 14 Pages.
Non-Final Office Action for U.S. Appl. No. 14/651,988, mailed Jun. 23, 2016, 16 Pages.
Non-Final Office Action for U.S. Appl. No. 14/970,945, mailed Feb. 12, 2016, 19 Pages.
Non-Final Office Action for U.S. Appl. No. 15/678,246, dated Sep. 5, 2018, 16 Pages.
Noord J.A., et al., "Comparison of Tiotropium Once Daily, Formoterol Twice Daily and Both Combined Once Daily in Patients With COPD, "The European Respiratory Journal, 2005, vol. 26(2), pp. 214-222.
Notice of Allowance for U.S. Appl. No. 14/651,988, mailed Nov. 16, 2016, 8 Pages.
Notice of Allowance for U.S. Appl. No. 14/970,945, mailed Jan. 11, 2017, 53 Pages.
Notice of Allowance for U.S. Appl. No. 14/970,945, mailed Apr. 20, 2017, 7 Pages.
Opposition for European Patent No. 2506844, by Dr. Markus Brewer of Henkele Breuer Partner, filed Sep. 19, 2018, 26 Pages.
Opposition for European Patent No. 2506844, by Sima Patent Lisanslama Hizmetleri Ltd STI, filed Sep. 20, 2018, 13 Pages.
Opposition for the European Application No. 09779096.8, published as EP2400950, by Sandoz AG, filed Feb. 24, 2020. 46 Pages.
PB62882EP official action dated Aug. 9, 2012, 7 pages.
Prat M., et al., "Discovery of Novel Quatemary Ammonium Derivatives of (3R)-Quinuclidinol Esters As Potent and Long-Acting Muscarinic Antagonists with Potential for Minimal Systemic Exposure After Inhaled Administration: Identification of (3R)-3-{[Hydroxy(di-2-thienyl)acetyl]oxy}-1-(3-phenoxypropyl)-1-azoniabicyclo[2.2.2]octane Bromide (Adlidinium Bromide)," Journal of Medicinal Chemistry, 2009, vol. 52, pp. 5076-5092.
PUBCHEM: "Umeclidinium Bromide | C29H34BrNO2," National Center for Biotechnology Information, Compound, Database accession No. CID 11519069, Oct. 26, 2006, 24 Pages, Retrieved from URL: https://pubchem.ncbi.nlm.nih.gov/compound/11519069.
Allen A., et al., "Fluticasone Furoate (FF) A Novel Inhaled Corticosteroid (ICS) Demonstrates Prolonged Lung Absorption Kinetics in Man," American Journal of Respiratory and Critical Care Medicine, American Thoracic Society 2010 International Conference, Abstract, D21 Asthma Therapy: New Targets, New Tricks, 2010, 2 Pages, DOI: http://dx.doi.org/10.1164/ajrcom-conference.2010.181.1MeetingAbstracts.A5408.
Amendment filed for U.S. Appl. No. 13/819,184, mailed Feb. 3, 2015, 6 Pages.
Annex to Patentee's Response to the Oppositions—Case Law Discussion, 11 Pages.
Anonymous, "View of NCT01673624 on Apr. 6, 2012," ClinicalTrials.gov, 2012, 4 Pages.
Anoro., "Summary of Product Characteristics," Annex, pp. 39.
Ball D.I., et al., "Salmeterol, a Novel, Long-acting Beta 2-adrenoceptor Agonist: Characterization of Pharmacological Activity in Vitro and in Vivo, "British Journal of Pharmacology, 1991, vol. 104(3), pp. 665-671.
Barnes P.J., "ABC of Chronic Obstructive Pulmonary Disease: Future Treatments," BMJ, Jul. 29, 2006, vol. 333, pp. 246-248, XP009083676.
Barnes P.J., "The Pharmacological Properties of Tiotropium," Chest, 2000, vol. 117, No. 2, pp. 63S-66S.
Barnes P.J., "The Role of Anticholinergics in Chronic Obstructive Pulmonary Disease, " The American Journal of Medicine, 2004, vol. 117, Issue No. 12A, pp. 24S-32S.
Bateman E., et al., "Efficacy And Safety of the Long-acting Muscarinic Antagonist GSK233705 Delivered Once Daily in Patients with COPD," The Clinical Respiratory Journal, 2012, vol. 6, pp. 248-257.

(56) References Cited

OTHER PUBLICATIONS

Battram C., et al., "In Vitro and in Vivo Pharmacological Characterization of 5-((R)-2-(5,6-diethyl-indan-2-ylamino)-1-hydroxyethyl]-8-hydroxy-1h-quinolin-2-one (Indacaterol), a Novel Inhaled Beta(2) Adrenoceptor Agonist With a 24-h Duration of Action, "The Journal of Pharmacology and Experimental Therapeutics, 2006, vol. 317(2), pp. 762-770.
Bleecker E.R., et al., "Consistently Favorable Safety Profile Of Fluticasone Furoate (ff), A Once-Daily (od) Inhaled Corticosteroid (ics), Across A Range Of Treatment Steps In Patients With Uncontrolled Asthma," American Thoracic Society International Conference Abstracts: A31 Optimizing Therapeutic Strategies in Airways Disease, May 15, 2011, 2 Pages, XP055307361.
British National Formulary 58, Sep. 2009, RPS Publishing, London, p. 168, 3 Pages.
British National Formulary: "BNF 56," Respiratory system, London, Sep. 2008, pp. 150-151, (4 Pages), OPP D35.
Casarosa P., et al., "Preclinical Evaluation of Long-Acting Muscarinic Antagonists: Comparison of Tiotropium and Investigational Drugs, " The Journal of Pharmacology and Experimental Therapeutics, 2009, vol. 330, No. 2, pp. 660-668.
Cazzola M., "Aclidinium Bromide, A Novel Long-acting Muscarinic M3 Antagonist for the Treatment of COPD," Current Opinion in Investigational Drugs, 2009, vol. 10, No. 5, pp. 482-490.
Cazzola M., "Current Opinion: Pharmacological Approaches in Asthma and COPD," Breathe, Sep. 1, 2009, vol. 6, No. 1, pp. 25-35, XP055943110, ISSN: 1810-6838, DOI: 10.1183/18106838.0601. 024.
Cazzola M., et al., "Emerging Inhaled Bronchodilators: An Update," European Respiratory Journal, Jan. 1, 2009, vol. 34, No. 3, pp. 757-769, XP055697899, DOI: 10.1183/09031936.00013109.
Cazzola M., et al., "Outcomes for COPD Pharmacological Trials: From Lung Function to Biomarkers," European Respiratory Journal, 2008, vol. 31, No. 2, pp. 416-468.
Cazzola M., et al., "Pharmacology and Therapeutics of Bronchodilators, "Pharmacological Reviews, 2012, vol. 64 (3), pp. 450-504.
Cazzola M., et al., "The Effective Treatment of COPD: Anticholinergics and What Else?," Drug Discovery Today; Therapeutic Strategies, 2006, vol. 3, No. 3, pp. 277-286, XP005777432.
Clinicaltrials: "History of Changes for Study: NCT00976144—Safety, Tolerability, Pharmacokinetic and Pharmacodynamic Effects of GSK573719 (LAMA) and GW642444 (LABA) Administered Individually and Concurrently in Healthy Japanese Subjects (DB2113208)," Clinicaltrials.gov, Sep. 11, 2009, pp. 1-5 (6 Pages), XP055943101, [Retrieved on Jul. 15, 2022] Retrieved from URL: https://clinicaltrials.gov/ct2/history/NGT00976144A=1B=1C=merged#StudyPageTop.
Clinicaltrials.Gov: "A Randomized, Single-dose, Dose-ascending, Double Blind, Placebo-controlled, 5-way Crossover Study to Investigate the Safety, Tolerability, Pharmacokinetics and Pharmacodynamics of Inhaled Doses of GW642444M With Magnesium Stearate in Asthmatic Patients, " Identifier NCT00463697, Jul. 15, 2010, 4 Pages, Opp D29, Retrieved from URL: https://clinicaltrials.gov/ct2/history/NCT00463697?V_7=View#StudyPageTop.
Clinicaltrials.Gov: "A Randomized, Single-Dose, Dose-Ascending, Double Blind, Placebo-Controlled, 5-Way Crossover Study to Investigate the Safety, Tolerability, Pharmacokinetics and Pharmacodynamics of Inhaled Doses of GW642444M With Magnesium Stearate in Asthmatic Patients, " Identifier NCT00463697, Oct. 15, 2008, 3 Pages, OPP D28, Retrieved from URL: https://clinicaltrials.gov/ct2/history/NCT00463697V_5=View#StudyPageTop.
Clinicaltrials.Gov: A Study to Assess the Safety and Tolerability of Once Daily Inhaled Doses of GSK573719 Made With Magnesium Stearate in Subjects With Chronic Obstructive Pulmonary Disease(COPD) for 7 Days, Clinical Study NCT00732472, Version 6, Aug. 27, 2009, pp. 1-7.
Clinicaltrials.Gov: "Efficacy And Safety Of GW642444M Comparing Placebo In Adolescent And Adult Subjects With Persistent Asthma," NCT00600171, OPP-D59, Jan. 22, 2009, 17 Pages, [Retrieved on Mar. 9, 2020] Retrieved from URL: https://clinicaltrials.govict2/show/NCT00600171.
Combinations of A Muscarinic Receptor Antagonist And A Beta-2 Adrenoreceptor Agonist for U.S. Appl. No. 14/970,945, filed Dec. 16, 2015, 49 Pages.
Communication Pursuant to Article 94(3) EPC for European Application No. 09779096.8, published as EP2400950, mailed Aug. 9, 2012, 7 Pages.
Consent From Concerning Clinical Study NCT00606684, Nov. 28, 2007, pp. 1-24.
Consent From Concerning Clinical Study NCT00732472, ICF Version No. 1.2, Aug. 22, 2008, pp. 1-26.
Consent From Concerning Clinical Study NCT00976144, Version 2, Jul. 15, 2009, pp. 1-20.
Co-Pending U.S. Appl. No. 13/819,184, filed Feb. 26, 2013. 89 Pages.
Co-Pending U.S. Appl. No. 15/678,246, filed Aug. 16, 2017, 43 Pages.
Datasheet for Decision Case No. T 0484/16, 2019, 33 Pages.
Datasheet for Decision Case No. T 0488/16, 42 Pages.
Datasheet for Decision Case No. T 2015/20, 2021, 23 Pages.
Datasheet for Decision Case No. T0106/07, 22 Pages,.
Datasheet for Decision Case No. TO184/16, 33 Pages.
Datasheet for Decision Case No. T0293/07, 44 Pages.
Datasheet for Decision Case No. T0296/93, 42 Pages.
Datasheet for Decision Case No. T0334/92, 14 Pages.
Datasheet for Decision Case No. T0383/10, 28 Pages.
Datasheet for Decision Case No. T0847/07, 37 Pages.
Datasheet for the Decision for European Case No. T 0237/15-3.3. 01, dated Jan. 28, 2019, 20 Pages.
Datasheet for the Decision for European Case No. T 0712/13-3.3. 01, dated Mar. 1, 2018, 58 Pages, OPP D31.
Datasheet for the Decision for European Case No. T 950/13-3.03. 01, dated Feb. 3, 2017, 27 Pages, OPP D27.
Datasheet for the Decision of Sep. 13, 2017 for the European Application No. 05012711.7, Published as EP1591122, Case No. T 0239/16-3.3.01, OPP 3, D6, 43 Pages.
Decision of Technical Board of Appeal 3.3.02 of Sep. 18, 2014, Case No. T 0484/09-3.3.02, 23 Pages.
Decision of the Opposition Division dated Apr. 13, 2016 in respect of EP1931350.
"Expert Panel Report 3; Guidelines for the Diagnosis and Management of Asthma," National Institutes of Health, National Heart, Lung and Blood Institue, Opp 3, D7, Aug. 28, 2007, 72 Pages.

* cited by examiner

COMBINATIONS OF A MUSCARINIC RECEPTOR ANTAGONIST AND A β-2 ADRENORECEPTOR AGONIST

FIELD OF THE INVENTION

This invention relates to pharmaceutical products and compositions for use in the treatment of chronic obstructive pulmonary disease (COPD), asthma and related diseases.

More particularly this invention relates to the combination of a muscarinic receptor antagonist and a beta-2 adrenoreceptor agonist, and the use of said combination in treating diseases mediated via the M3 muscarinic acetylcholine receptor and/or the beta-2 adrenoreceptor.

More particularly this invention is concerned with novel pharmaceutical combination products comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate and 4-[hydroxy(diphenyl)methyl]-1-{2-[(phenylmethyl)oxy]ethyl}-1-azoniabicyclo[2,2,2]octane bromide and the use of said combination products in medicine, particularly in treating diseases mediated via the M3 muscarinic acetylcholine receptor and/or the beta-2 adrenoreceptor, for example in the prophylaxis and treatment of inflammatory or respiratory tract diseases.

BACKGROUND OF THE INVENTION

Selective β2-adrenoreceptor agonists have been used in the prophylaxis and treatment of clinical conditions for which a bronchodilating agent has been indicated. Such conditions include diseases associated with airflow obstruction such as chronic obstructive pulmonary diseases (COPD) (e.g. chronic and wheezy bronchitis, emphysema), asthma, respiratory tract infection and upper respiratory tract disease (e.g. rhinitis, including seasonal and allergic rhinitis).

In particular, asthma and other related disorders are typically treated with beta-2 adrenergic receptor agonists (beta-2 agonists) as they provide a bronchodilator effect to the patient, resulting in relief from the symptoms of breathlessness. Within the beta-2 agonist class there are presently available short acting compounds for immediate relief, such as salbutamol, biltolterol, pirbuterol and terbutaline. There are also longer acting compounds commercially available, such as salmeterol and formoterol. Salmeterol is available by prescription for use twice daily in the treatment of asthma.

Over the last two decades, inhaled anticholinergic agents have become well established as well-tolerated and effective bronchodilators for the treatment of COPD. Treatment with anticholinergics significantly improves FEV (forced expiratory volume in 1 second) resting and dynamic lung hyperinflation, symptoms and exercise capacity, and reduces COPD exacerbations. Currently, only a few inhaled anticholinergic bronchodilators are available: the short-acting ipratropium bromide (ipratropium; dosed four-times-a-day) and oxitropium bromide, and the long-acting tiotropium bromide (tiotropium; dosed once-daily).

WO 03/024439 describes compounds of the general formula;

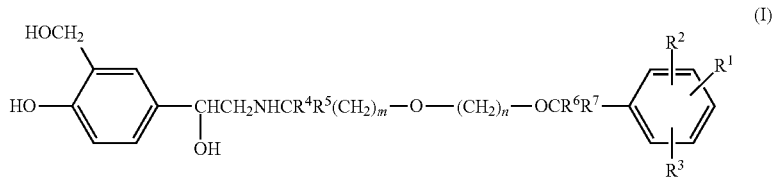

and salts, solvates, and physiologically functional derivatives thereof.

The compound 4-{(1R)-2-[(6-{2-[(2,6-dichlorobenzyl)oxy]ethoxy}hexyl)amino]-1-hydroxyethyl}-2-(hydroxymethyl)phenol is specifically described in WO03/024439, as are pharmaceutically acceptable salts thereof, in particular the acetate, triphenylacetate, α-phenylcinnamate 1-naphthoate and (R)-mandelate salts. WO 2005/104745 describes compounds of the formulae:

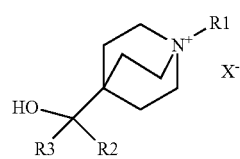

WO2005/104745 specifically describes the compound 4-[hydroxy(diphenyl)methyl]-1-{2-[phenylmethyl)oxy]ethyl}-1-azoniabicyclo[2.2.2]octane bromide.

SUMMARY OF THE INVENTION

In a first aspect the present invention provides a novel pharmaceutical combination product comprising the therapeutic agents:

a) a compound of the formula:

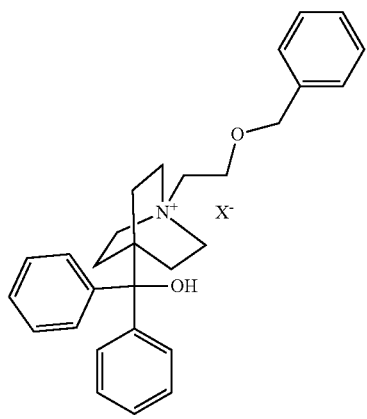

Compound (I)

wherein
X⁻ is a pharmaceutically acceptable anion;
and
b) a compound of the formula:

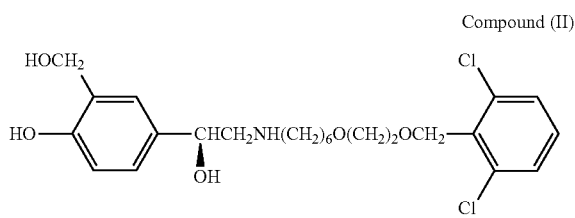

Compound (II)

or a pharmaceutically acceptable salt thereof.

Hereinafter, Compound (II) may refer to the free base depicted above, and/or one or more salts thereof, as dictated by the context.

In one embodiment the pharmaceutical combination product comprises 4-{(1R)-2-[(6-{2-[(2,6-dichlorobenzyl)oxy]ethoxy}hexyl)amino]-1-hydroxyethyl}-2-hydroxymethyl)phenol triphenylacetate and 4-[hydroxy(diphenyl)methyl]-1-{2-[(phenylmethyl)oxy]ethyl}-1-azoniabicyclo[2.2.2]octane bromide.

In one embodiment 4-{(1R)-2-[(6-{2-[(2,6-dichlorobenzyl)oxy]ethoxy}hexyl)amino]-1-hydroxyethyl}-2-(hydroxymethyl)phenol triphenylacetate and 4-[hydroxy(diphenyl)methyl]-1-{2-[(phenylmethyl)oxy]ethyl}-1-azoniabicyclo[2.2.2]octane bromide are the sole active ingredients in said pharmaceutical combination product.

In another embodiment the pharmaceutical combination product of Compound (I) and Compound (II) additionally comprises an inhaled corticosteroid.

This invention also provides for use of the pharmaceutical combination product in the manufacture of a medicament for the treatment of conditions for which administration of one or more of the therapeutic compounds is indicated.

In one embodiment the use is for the manufacture of a medicament for the treatment of inflammatory or respiratory tract diseases, by simultaneous or sequential administration of Compound (I) and Compound (II).

In another embodiment the use is for the manufacture of a medicament for the treatment of chronic obstructive pulmonary disease (COPD) and/or asthma, by simultaneous or sequential administration of Compound (I) and Compound (II).

The invention also provides said pharmaceutical combination product for use in the treatment of inflammatory or respiratory tract diseases, such as chronic obstructive pulmonary disease (COPD) and/or asthma.

Another embodiment of the invention is a method for the treatment of inflammatory or respiratory tract diseases, comprising administering either sequentially or simultaneously, to a patient in need thereof, a pharmaceutical combination product comprising Compound (I) and Compound (II).

In one embodiment of the invention the inflammatory or respiratory tract disease is selected from the group consisting of chronic obstructive pulmonary disease, chronic bronchitis, asthma, chronic respiratory obstruction, pulmonary fibrosis, pulmonary emphysema, allergic rhinitis, small airways disease, bronchiectasis and cystic fibrosis.

In another embodiment of the invention the pharmaceutical combination product may be used for the treatment of inflammatory or respiratory tract diseases, and more specifically the treatment of chronic obstructive pulmonary disease (COPD) and/or asthma by simultaneous or sequential administration of Compound (I) and Compound (II).

DETAILED DESCRIPTION OF THE INVENTION

The present invention is directed to a pharmaceutical combination product comprising
a) a compound of formula:

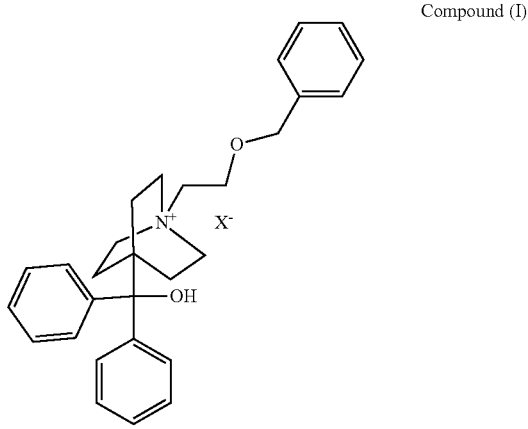

Compound (I)

wherein
X⁻ is a pharmaceutically acceptable anion;
and
b) a compound of formula:

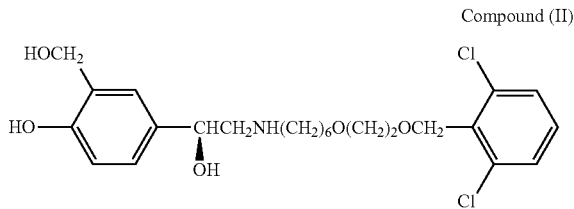

Compound (II)

or a pharmaceutically acceptable salt thereof.

The pharmaceutically acceptable anion depicted by X may be selected from chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate. In one embodiment the pharmaceutically acceptable anion X⁻ is bromide.

For purposes herein, the structural formula for the quaternary moiety (cation) of Compound (I) is also referred to as 4-[hydroxy(diphenyl)methyl]-1-{2-[(phenylmethyl)oxy]ethyl}-1-azoniabicyclo[2,2,2]octane.

In one embodiment of the invention Compound (I) is 4-[hydroxy(diphenyl)methyl]-1-{2-[(phenylmethyl)oxy]ethyl}-1-azoniabicyclo[2.2.2]octane bromide (also referred to herein as Compound (I) bromide).

Pharmaceutically acceptable acid addition salts of Compound (II) include those formed from hydrochloric, hydrobromic, sulphuric, citric, tartaric, phosphoric, lactic, pyruvic, acetic, trifluoroacetic, triphenylacetic, phenylacetic, substituted phenyl acetic eg. methoxyphenyl acetic, sulphamic, sulphanilic, succinic, oxalic, fumaric, maleic, malic, glutamic, aspartic, oxaloacetic, methanesulphonic, ethanesulphonic, arylsulponic (for example p-toluenesulphonic, benzenesulphonic, naphthalenesulphonic or naphthalenedisulphonic), salicylic, glutaric, gluconic, tricarballylic, mandelic, cinnamic, substituted cinnamic (for example, methyl, methoxy, halo or phenyl substituted cinnamic, including 4-methyl and 4-methoxycinnamic acid and α-phenyl cinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, bezeneacrylic (for example 1,4-benzenediacrylic) and isethionic acids.

In one embodiment the pharmaceutically acceptable salt of Compound (II) is selected from the acetate, 1-naphthoate and (R) mandelate salts.

In another embodiment the pharmaceutically acceptable salt of Compound (II) is the a-phenylcinnamate salt.

In another embodiment the pharmaceutically acceptable salt of Compound (II) is the triphenylacetate salt.

The structural formula shown above for Compound (II) may be named as 4-{(1R)-2-[(6-{2-[(2,6-dichlorobenzyl)oxy]ethoxy}hexyl)amino]-1-hydroxyethyl}-2-(hydroxymethyl)phenol.

In one embodiment of the invention Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate (also referred to as Compound (II) triphenylacetate).

In one embodiment the pharmaceutical combination product of the invention comprises 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In another embodiment the pharmaceutical combination product of Compound (I) and Compound (II) additionally comprises an inhaled corticosteroid, e.g. fluticasone propionate, mometasone furoate, budesonide or 6a,9a-difluoro-17a-[(2-furanylcarbonyl)oxy]-11β-hydroxy-I 6a-methyl-3-oxo-androsta-1,4-diene-17p-carbothioic acid S-fluoromethyl ester (fluticasone furoate).

In one embodiment said pharmaceutical combination product comprises 4-[hydroxy(diphenyl)methyl]-1-{2-[(phenylmethyl)oxy]ethyl}-1-azoniabicyclo[2.2.2]octane bromide, 4-{(1R)-2-[(6-{2-[(2,6-dichlorobenzyl)oxy]ethoxy}hexyl)amino]-1-hydroxyethyl}-2-(hydroxymethyl)phenol triphenylacetate and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

In one embodiment, the pharmaceutical combination product of the invention comprises 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate as the sole active ingredients.

Compound (I), specifically 4-[hydroxy(diphenyl)methyl]-1-{2-[(phenylmethyl)oxy]ethyl}-1-azoniabicyclo[2.2.2]octane bromide has been the subject of studies in animal models, and in humans, and has been found to be a long acting high-affinity pan-active muscarinic receptor antagonist which has potential for once-daily administration.

Compound (II), specifically 4-{(1R)-2-[(6-{2-[(2,6-dichlorobenzyl)oxy]ethoxy}hexyl)amino]-1-hydroxyethyl}-2-(hydroxymethyl)phenol and its salts has been extensively tested in animal and human studies and has been found to demonstrate sustained bronchodilation over a 24 hour period in conjunction with a favourable safety profile and thus has the potential for once-daily administration.

Compound (I) and Compound (II), and the combination thereof, are considered to have potential in the treatment of inflammatory or respiratory tract diseases such as chronic obstructive pulmonary disease, chronic bronchitis, asthma, chronic respiratory obstruction, pulmonary fibrosis, pulmonary emphysema, allergic rhinitis, small airways disease, bronchiectasis and cystic fibrosis.

COPD is a chronic disease characterised by airways obstruction and reduced maximum expiratory flow from the lungs that manifests as persistent daily symptoms, such as shortness of breath (dyspnoea), and limitation of the ability to perform daily activities or exertion. Furthermore, there are periodic exacerbations of the condition that result in worsening of the day-today symptoms and activity limitation, and can also lead to hospitalisation of the patient because of the seventy of the worsening symptoms/limitation. In addition, there is a progressive decline in lung function (disease progression) over several years.

Bronchodilator treatment in COPD includes but is not necessarily limited to reducing symptoms, particularly dyspnoea, to allow a patient to undertake more daily activities and other activities that require exertion, and preventing exacerbations.

Asthma is a chronic condition, which is characterised by widespread, variable and reversible airflow obstruction. Symptoms include coughing, wheezing, breathlessness and/or a tight feeling in the chest. Asthma attacks are generally caused by exposure to a trigger, such as pollen, dust or other allergens, which causes constriction of the airways (bronchoconstriction). It will be appreciated that a subject suffering from a condition such as asthma, may variously from time to time display no overt symptoms of the condition, or may suffer from periodic attacks during which symptoms are displayed or may experience exacerbations or worsening of the condition. In this context the term 'treatment' is intended to encompass prevention of such periodic attacks or exacerbations of the existing condition. Such treatment may be referred to as 'maintenance treatment' or 'maintenance therapy'.

The amounts of Compound (I) and Compound (II), and in one embodiment of the invention, 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate, required to achieve a therapeutic effect will, of course, vary with the route of administration, the subject under treatment, the particular disorder or disease being treated, and the severity of the disease. In one embodiment, the route of administration is by inhalation via the mouth or nose. In a further embodiment, the route of administration is by inhalation via the mouth.

In one embodiment Compound (I), and specifically (4-[hydroxy(diphenyl)methyl]-1-{2-[(phenylmethyl)oxy]ethyl}-1-azoniabicyclo[2.2.2]octane bromide, may be administered by inhalation at a dose of from about 1 mcg to about 1000 mcg/daily, e.g. 100, 250 or 500 mcg per day. In a further embodiment, Compound (I) and specifically (4-[hydroxy(diphenyl)methyl]-1-{2-[(phenylmethyl)oxy]ethyl}-1-azoniabicyclo[2,2,2]octane bromide may be administered by inhalation at a dose of 62.5 mcg or 125 mcg per day. In general Compound (I) will be administered as a once-daily dose.

In a further embodiment, Compound (I), and specifically (4-[hydroxy(diphenyl)methyl]-1-{2-[(phenylmethyl)oxy]ethyl}-1-azoniabicyclo[2.2.2]octane bromide, may be administered by inhalation, once-daily, at a dose of 62.5 mcg per day.

In a further embodiment, Compound (I), and specifically (4-[hydroxy(diphenyl)methyl]-1-{2-[(phenylmethyl)oxy]ethyl}-1-azoniabicyclo[2.2.2]octane bromide, may be administered by inhalation, once-daily, at a dose of 125 mcg per day.

Compound (II) may for example be administered by inhalation at a dose of from about 1 mcg to about 400 mcg/day (calculated as the free base). In one embodiment Compound (II), and specifically 4-{(1R)-2-[(6-{2-[(2,6-dichlorobenzyl)oxy]ethoxy}hexyl)amino]-1-hydroxyethyl}-2-(hydroxymethyl)phenol triphenylacetate, may be administered by inhalation at a dose of from about 1 mcg to 100 mcg/day, for example 3, 6.25, 12.5, 25, 50 or 100 mcg/day (calculated as the free base). In general Compound (II) will be administered as a once-daily dose. In one embodiment Compound (II) may be administered by inhalation at a dose of 12.5 mcg/day. In another embodiment Compound (II) may be administered by inhalation at a dose of 25 meg/day. In another embodiment Compound (II) may be administered by inhalation at a dose of 50 meg/day.

In a further embodiment, 4-{(1R)-2-[(6-{2-[(2,6-dichlorobenzyl)oxy]ethoxy}hexyl)amino]-1-hydroxyethyl}-2-(hydroxymethyl)phenol triphenylacetate, may be administered by inhalation, once-daily, at a dose of 25 mcg per day.

In a further embodiment, the present invention provides a pharmaceutical combination product for once-daily administration by inhalation, comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate at a dose of 25 mcg per day, and (4-[hydroxy(diphenyl)methyl]-1-{2-[(phenylmethyl)oxy]ethyl}-1-azoniabicyclo[2.2.2]octane bromide at a dose of 125 mcg per day.

In a further embodiment, the present invention provides a pharmaceutical combination product for once-daily administration by inhalation, comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate at a dose of 25 mcg per day, and (4-[hydroxy(diphenyl)methyl]-1-{2-[(phenylmethyl)oxy]ethyl}-1-azoniabicyclo[2.2.2]octane bromide at a dose of 62.5 mcg per day.

When the combination additionally includes an inhaled corticosteroid, this may be used at doses compatible with those known for monotherapy. When the inhaled corticosteroid is fluticasone furoate this may be administered by inhalation at a dose of from about 25 mcg to about 800 mcg daily, and if necessary in divided doses. Thus, the daily dose of fluticasone furoate may be for example 25, 50, 100, 200, 300, 400, 600 or 800 meg, in general as a once-daily dose. In one embodiment, the daily dose of fluticasone furoate is 100 mcg. In a further embodiment, the daily dose of fluticasone furoate is 50 mcg.

The individual compounds of the pharmaceutical combination product as described herein may be administered either sequentially or simultaneously in separate or combined pharmaceutical formulations/compositions. Thus Compound (I) and Compound (II) may for example, be formulated separately and presented in separate packs or devices, or said individually formulated components may be presented in a single pack or device. Where appropriate, the individual compounds may be admixed within the same formulation, and presented as a fixed pharmaceutical combination. In general such formulations will include pharmaceutical carriers or excipients as described hereinafter, but combinations of the compounds without any excipients are also within the ambit of this invention. In one embodiment, the individual compounds of the pharmaceutical combination product may be administered simultaneously in a combined pharmaceutical formulation or composition.

When the pharmaceutical combination product additionally includes an inhaled corticosteroid, eg 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) this may likewise be formulated separately, either with or without one or more pharmaceutical carriers or excipients, and presented for either sequential or simultaneous administration, or the inhaled corticosteroid may be admixed with either Compound (I) and/or Compound (II). 6α,9α-Difluoro-17α-[(2-furanylcarbonyl)oxy]-11β-hydroxy-I 6α-methyl-3-oxo-androsta-1,4-diene-17β-carbothioic acid S-fluoromethyl ester may be formulated for example as described in WO02/12265, or as described hereinafter.

In further aspects the invention therefore provides:

A pharmaceutical combination product comprising Compound (I) and Compound (II) presented separately for sequential or simultaneous administration;

A pharmaceutical combination product comprising Compound (I) and Compound (II) presented separately but held in the same pack or device, for sequential or simultaneous administration; and A pharmaceutical combination product comprising Compound (I) and Compound (II) in admixture with each other for simultaneous administration.

In each case, each of Compound (I) and/or Compound (II) may be formulated with or without pharmaceutical carriers or excipients.

The present invention further provides a pharmaceutical combination product comprising Compound (I) and Compound (II) wherein at least one of Compound (I) and Compound (II) is formulated with a pharmaceutically acceptable carder or excipient.

The present invention further provides a pharmaceutical combination product comprising Compound (I) and Compound (II) wherein each of Compound (I) and Compound (II) is formulated with a pharmaceutically acceptable carrier or excipient.

In one embodiment of this invention compositions of Compounds (I) and (II) include those suitable for inhalation, including fine particle powders, or mists which may be generated and administered by means of various types of inhalers for example, reservoir dry powder inhalers, unit-dose dry powder inhalers, pre-metered multi-dose dry powder inhalers, nasal inhalers or pressurized metered dose inhalers, nebulisers or insufflators.

The compositions may be prepared by any of the methods well known in the art of pharmacy. In general, said methods include the step of bringing the active ingredient(s) into association with the carrier which constitutes one or more accessory ingredients. In general the compositions are prepared by uniformly and intimately bringing into association the active ingredient with liquid carriers or finely divided solid carriers or both and then, if necessary, shaping the product into the desired composition.

Powder compositions generally contain a powder mix for inhalation of the active ingredient and a suitable powder base (carrier/diluent/excipient substance) such as mono-, di or poly-saccharides (e.g. lactose or starch). Use of lactose is preferred. The lactose may be for example anhydrous lactose or a-lactose monohydrate. In one embodiment, the carrier is a-lactose monohydrate. Dry powder compositions may also include, in addition to the active ingredient and carder, a further excipient (eg a ternary agent) such as a sugar ester, calcium stearate or magnesium stearate.

Alternatively, the active ingredient may be presented without excipients. For the avoidance of doubt use of the term 'composition' or 'formulation' herein refers to the active ingredients either with or without excipients or carriers.

The present invention further provides a pharmaceutical combination product comprising Compound (I) and Compound (II) wherein at least one of Compound (I) and Compound (II) is formulated with a pharmaceutically acceptable carrier and a ternary agent.

The present invention further provides a pharmaceutical combination product comprising Compound (I) and Compound (II) wherein Compound (II) is formulated with a pharmaceutically acceptable carrier and a ternary agent.

In another embodiment the present invention further provides a pharmaceutical formulation comprising a combination of Compound (I) and Compound (H) wherein both Compounds are formulated with a pharmaceutically acceptable carrier and a ternary agent.

The present invention further provides a pharmaceutical combination product for inhaled administration comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate and (4-[hydroxy(diphenyl)methyl]-{2-[(pheynylmethyl)oxy]ethyl}-1-azoniabicyclo[2,2,2]octane bromide each formulated separately with a pharmaceutically acceptable carrier and a ternary agent, but held in the same pack or device, for sequential or simultaneous administration.

In one embodiment said ternary agent is magnesium stearate.

The present invention further provides a pharmaceutical combination product for inhaled administration comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate and (4-[hydroxy(diphenyl)methyl]-1-{2-[(pheynylmethyl)oxy]ethyl}-1-azoniabicyclo[2,2,2]octane bromide each formulated separately with lactose, as a pharmaceutically acceptable carrier, and magnesium stearate, as a ternary agent, but held in the same pack or device, for sequential or simultaneous administration.

The compositions may be presented in unit dosage form. Dry powder compositions for topical delivery to the lung by inhalation may, for example, be presented in capsules and cartridges of for example gelatine, or busters of for example laminated aluminium foil, for use in an inhaler or insufflator.

Each capsule, cartridge or blister may generally contain between 1 mcg-1000 mcg, e.g. 100 to 500 mcg of Compound (I) and/or between 1 mcg-400 mcg, e.g 1 to 100 mcg of Compound (II). Packaging of the formulation may be suitable for unit dose or multi-dose delivery. As indicated above Compound (I) and Compound (II) may be formulated independently or in admixture. Said compounds may thus be incorporated in separate unit doses or may be combined in a single unit dose with or without additional excipients as deemed necessary.

In a further embodiment, each capsule, cartridge or blister may contain 125 mcg or 62.5 mcg of Compound (I) and/or 25 mcg of Compound (II).

In yet a further embodiment, each capsule, cartridge or blister may contain 125 mcg or 62.5 mcg of (4-[hydroxy(diphenyl)methyl]-1-{2-[(phenylmethyl)oxy]ethyl}-1-azoniabicyclo[2.2.2]octane bromide and/or 25 mcg of 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In one embodiment, a composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline. The DISKUS™ inhalation device is, for example, described in GB 2242134A.

A dry powder inhalable composition, may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ of AstraZeneca, TWISTHALER™ of Schering and CLICKHALER™ of Innovata.

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ of GlaxoSmithKline and HANDHALER™ of Boehringer Ingelheim.

A dry powder composition may also be presented in a delivery device which permits separate containment of Compound (i) and Compound (II) optionally in admixture with one or more excipients. Thus, for example, the individual compounds of the combination are administrable simultaneously but are stored separately, e.g. in separate pharmaceutical compositions, for example as described in WO 2003/061743 A1, WO 2007/012871 A1 and/or WO2007/068896. In one embodiment a delivery device permitting separate containment of actives is an inhaler device having two medicament packs in peelable blister strip form, each pack containing pre-metered doses in blister pockets arranged along its length. Said device has an internal indexing mechanism which, each time the device is actuated, peels opens a pocket of each strip and positions the packs so that each newly exposed dose of each pack is adjacent a manifold which communicates with a mouthpiece of the device. When the patient inhales at the mouthpiece, each dose is simultaneously drawn out of its associated pocket into the manifold and entrained via the mouthpiece into the patient's respiratory tract. Thus, each time the device is used, the patient is administered a combination therapy consisting of a dose from each medicament pack. A further device that permits separate containment of different compounds is DUOHALER™ of Innovate.

In a further embodiment, the present invention provides a dry powder inhaler (Inhaler 1) comprising two compositions presented separately, wherein a first composition comprises
 i. 4-[hydroxy(diphenyl)methyl]-1-{2-[(phenylmethyl)oxy]ethyl}-1-azoniabicyclo[2.2.2]octane bromide, and
 ii. lactose, and
 iii. magnesium stearate at an amount of about 0.6% w/w based on the total weight of the first composition;
and a second composition comprises
 i. 4-{(1R)-2-[(6-{2-[(2,6-dichlorobenzyl)oxy]ethoxy}hexyl)amino]-1-hydroxyethyl}-2-(hydroxymethyl)phenol triphenylacetate, and
 ii. lactose, and
 iii. magnesium stearate at an amount of about 1.0% w/w based on the total weight of the second composition.

In a further embodiment, the present invention provides Inhaler 1 wherein each composition is in unit dose form.

In a further embodiment, the present invention provides Inhaler 1 wherein the unit dose form is a capsule, cartridge or blister.

In a further embodiment, the present invention provides Inhaler 1 wherein 4-[hydroxy(diphenyl)methyl]-1-{2-[(phenylmethyl)oxy]ethyl}-1-azoniabicyclo[2.2.2]octane bromide is present in an amount of about 125 mcg/dose.

In a further embodiment, the present invention provides Inhaler 1 wherein 4-{(1R)-2-[(6-{2-[(2,6-dichlorobenzyl)oxy]ethoxy}hexyl)amino]-1-hydroxyethyl}-2-(hydroxymethyl)phenol triphenylacetate is present in an amount of about 25 mcg/dose.

In a further embodiment, the present invention provides Inhaler 1 wherein the second composition further comprises 6α,9α-difluoro-17α-[(2-furanylcarbonyl)oxy]-11β-hydroxy-16α-methyl-3-oxo-androsta-1,4-diene-17β carbothioic acid S-fluoromethyl ester (fluticasone furoate).

In a further embodiment, the present invention provides Inhaler 1 wherein 6α, 9α-difluoro-17α-[2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

Spray compositions for inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the pharmaceutical product and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid derivative e.g. as described in WO94/21229 and WO98/34596 and/or cosolvents e.g. ethanol. Pressurised formulations will generally be retained in a canister (e.g. an aluminium canister) dosed with a valve (e.g. a metering valve) and fitted into an actuator provided with a mouthpiece.

There is thus provided as a further aspect of the invention a pharmaceutical combination product comprising Compound (I) and Compound (II) formulated individually or in admixture, with a fluorocarbon or hydrogen-containing chlorofluorocarbon as propellant, optionally in combination with a surface-active agent and/or a co-solvent. According to another aspect of the invention, the propellant is selected from 1,1,1,2-tetrafluoroethane, 1,1,1,2,3,3,3-heptafluoro-n-propane and mixtures thereof.

Another aspect of the invention is a pharmaceutical combination product consisting of Compound (I) and Compound (II) formulated individually or in admixture, with a fluorocarbon or hydrogen-containing chlorofluorocarbon as propellant, optionally in combination with a surface-active agent and/or a cosolvent. In another embodiment of the invention the propellant is selected from 1,1,1,2-tetrafluoroethane, or 1,1,1,2,3,3,3-heptafluoro-n-propane and mixtures thereof.

Where appropriate compositions according to the invention may be buffered by the addition of suitable buffering agents.

Active ingredients for administration by inhalation desirably have a controlled particle size. The optimum particle size for inhalation into the bronchial system is usually 1-10 µM, preferably 2-5 µm, Particles having a size above 20 µm are generally too large when inhaled to reach the small airways. To achieve these particle sizes the particles of the active ingredient as produced may be size reduced by conventional means e.g. by micronization. The desired fraction may be separated out by air classification or sieving. Preferably, the particles will be crystalline.

Dry powder compositions according to the invention may comprise a carrier. The carrier when it is lactose, e.g. a-lactose monohydrate, may form from about 91 to about 99%, e.g. 97.7-99.0% or 91.0-99.2% by weight of the formulation. In general, the particle size of the carrier, for example lactose, will be much greater than the inhaled medicament within the present invention. When the carder is lactose it will typically be present as milled lactose, having a MMD (mass median diameter) of 60-90 µm.

The lactose component may comprise a fine lactose fraction. The 'fine' lactose fraction is defined as the fraction of lactose having a particle size of less than 7 µm, such as less than 6 µm, for example less than 5 µm. The particle size of the 'fine' lactose fraction may be less than 4.5 µm. The fine lactose fraction, if present, may comprise 2 to 10% by weight of the total lactose component, such as 3 to 6% by weight fine lactose, for example 4.5% by weight fine lactose.

Magnesium stearate, if present in the composition, is generally used in an amount of about 0.2 to 2%, e.g. 0.6 to 2% or 0.5 to 1.75%, e.g. 0.6%, 0.75%, 1%, 1.25% or 1.5% w/w, based on the total weight of the composition. The magnesium stearate will typically have a particle size in the range 1 to 50 µm, and more particularly 1-20 µm, −10 µm. Commercial sources of magnesium stearate include Peter Greven, Covidien/Mallinckodt and FACI.

In a further embodiment there is provided a pharmaceutical combination product comprising Compound (I) and Compound (II) wherein Compound (I) is (4-[hydroxy(diphenyl)methyl]-1-{2-[(phenylmethyl)oxy]ethyl}-1-azoniabicyclo[2.2.2]octane bromide and is presented as a dry powder composition containing magnesium stearate at an amount of 0.6% w/w based on the total weight of the composition.

In yet a further embodiment, there is provided a pharmaceutical combination product comprising Compound (I) and Compound (II) wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate and is presented as a dry powder composition containing magnesium stearate at an amount of 1.0% w/w based on the total weight of the composition.

Intranasal sprays may be formulated with aqueous or nonaqueous vehicles with the addition of agents such as thickening agents, buffer salts or acid or alkali to adjust the pH, isotonicity adjusting agents or anti-oxidants.

Solutions for inhalation by nebulization may be formulated with an aqueous vehicle with the addition of agents such as acid or alkali, buffer salts, isotonicity adjusting agents or antimicrobials. They may be sterilized by filtration or heating in an autoclave, or presented as a non-sterile product.

The invention also provides a method of preparing a pharmaceutical combination product as defined herein, the method comprising either:
  (a) preparing a separate pharmaceutical composition for administration of the individual compounds of the combination either sequentially or simultaneously, or
  (b) preparing a combined pharmaceutical composition for administration of the individual compounds together in the combination for simultaneous use, wherein the pharmaceutical composition comprises the combination together with one or more pharmaceutically acceptable carriers and/or excipients.

4-{(1R)-2-[(6-{2-[(2,6-dichlorobenzyl)oxy]ethoxy}hexyl)amino]-1-hydroxyethyl}-2-(hydroxymethyl)phenol, and its salts, including 4-{(1R)-2[(6-{2-[(2,6-dichlorobenzyl)oxy]ethoxy}hexyl)amino]-1-hydroxyethyl}-2-(hydroxymethyl)phenol triphenylacetate may be prepared as described in WO03/024439 (Example 78(i)), which is incorporated by reference herein.

4-[hydroxy(diphenyl)methyl]-1-{2-[(phenylmethyl)oxy]ethyl}-1-azoniabicyclo[2.2.2]octane bromide is described as Example 84, in WO2005/104745 which is incorporated by reference herein.

Clinical Studies

4-[hydroxy(diphenyl)methyl]-1-{2-[(phenylmethyl)oxy]ethyl}-1-azoniabicyclo[2.2.2]octane bromide 4-[hydroxy(diphenyl)methyl]-1-{2-[(phenylmethyl)oxy]ethyl}-1-azoniabicyclo[2.2.2]octane bromide has been found to be an effective long-acting potent, pan active anti-muscarinic bronchodilator which demonstrates slow reversibility at the human M3 receptor in vitro and long duration of action in vivo when administered directly to the lungs in pre-clinical models. The long duration of action of this compound identified using in vitro models, when administered via inhalation in animals, and subsequently in early phase studies in healthy volunteers and COPD subjects supports the potential for use of this compound as a once daily bronchodilator for COPD.

Several clinical pharmacology studies have been conducted using 4-[hydroxy(diphenyl)methyl]-1-{2-[(phenylmethyl)oxy]ethyl}-1-azoniabicyclo[2.2.2]octane bromide in both healthy volunteers and COPD patients to investigate the safety, tolerability, pharmacokinetics and pharmacodynamics of this compound. The bronchodilatory effects and duration of action of single inhaled doses of this compound as measured by plethysmography ($sG_{aw}$, $R_{aw}$) and spirometry ($FEV_1$) were assessed in some of the above noted studies. These studies showed clinically relevant bronchodilation and 24 h duration of action for the compound.

In one such study, designed to evaluate the safety, efficacy and pharmacokinetics of 4-[hydroxy(diphenyl)methyl]-1-{2-[(phenylmethyl)oxy]ethyl}-1-azoniabicyclo[2.2.2]octane bromide in subjects with COPD, five once-daily doses (62.5 mcg, 125 mcg, 250 mcg, 500 mcg and 1000 mcg), taken over a 14-day treatment period, produced statistically significant improvements in pulmonary function compared to placebo. All once-daily doses showed numerically greater improvement in trough $FEV_1$ than the open label tiotropium active control (18 mcg once-daily). In addition, this study confirmed that 4-[hydroxy(diphenyl)methyl]-1-{2-[(phenylmethyl)oxy]ethyl}-1-azoniabicyclo[2.2.2]octane bromide has a once-daily profile.

A further study evaluated the efficacy and safety of three doses (125 mcg, 250 mcg and 500 mcg) of 4-[hydroxy(diphenyl)methyl]-1-{2-[(phenylmethyl)oxy]ethyl}-1-azoniabicyclo[2,2,2]octane bromide administered once-daily via a dry powder inhaler over a 28 day period in subjects with COPD. This study confirmed that 4-[hydroxy(diphenyl)methyl]-1-{2-[(phenylmethyl)oxy]ethyl}-1-azoniabicyclo[2.2.2]octane bromide appears to be safe and efficacious, maintaining significant bronchodilation over twenty four hours.

Compound (II) (as the a-phenylcinnamate Salt or the Triphenylacetate Salt)

Compound (II) as the α-phenylcinnamate salt and the triphenylacetate salt has been studied in a number of clinical pharmacology studies, including single- and repeat-dose studies. In addition, these studies have evaluated Compound (II) formulated with lactose and either cellobiose octaacetate or magnesium stearate. In asthmatic patients, a statistically and clinically significant improvement in trough (24-hour) FEV1 was observed for all doses of Compound (II) tested, compared to placebo. Single doses of 25 μg to 100 μg of Compound (II) triphenylacetate (containing lactose and magnesium stearate) demonstrated 24 hour duration of action as assessed by a 200 mL or greater increase in mean 23 to 24 hour post-dose FEV1 versus placebo.

In COPD patients, treatment with 100 mcg and 400 mcg Compound (II) alpha-phenylcinnamate (with lactose alone) achieved a clinically relevant adjusted mean difference from placebo in weighted mean trough $FEV_1$ (22 to 24 hrs) of >100 mL Single doses of 25 μg to 100 μg of Compound (II) triphenylacetate (containing lactose and magnesium stearate) demonstrated 24 hour duration of action as assessed by a 190 mL or greater increase in mean 23 to 24 hour post-dose FEV1 versus placebo), Combination Therapy A combination of Compound (i) bromide and Compound (II) triphenylacetate has been administered to sixteen healthy Japanese volunteers, aged 20 to 65, as part of a clinical trial to assess the safety, tolerability, pharmacokinetics and pharmacodynamics of single inhaled doses of Compound (I) bromide and Compound (II) triphenylacetate as monotherapies and in combination. This study was a randomised, double blind, placebo-controlled, four-way crossover study wherein subjects received a single dose of:
  Compound (I) bromide (500 mcg dose),
  Compound (II) triphenylacetate (50 mcg dose),
  Compound (I) bromide (500 mcg dose) and Compound (II) triphenylacetate (50 mcg dose) concurrently, or
  placebo
at each of the four treatment periods. On enrolment into the study subjects were assigned to one of four treatment sequences based on a Williams design.

This clinical study in healthy Japanese volunteers, evaluated the effect of Compound (I) bromide (500 mcg dose) and Compound (II) triphenylacetate (50 mcg dose) administered as single inhaled doses and concurrently (Compound (I) bromide (500 mcg dose) and Compound (II) triphenylacetate (50 mcg dose)) on lung function parameters. Single inhaled doses and the combination administered using dry powder inhalers were found to be well tolerated. In this study $FEV_1$ values were recorded. $FEV_1$ values were higher for all treatment groups compared with placebo. The group dosed with Compound (I) bromide (500 mcg dose) and Compound (II) triphenylacetate (50 mcg dose) concurrently showing the largest difference relative to placebo.

Pharmaceutical Formulations

Preparation of Blends

Compound (1) Bromide

Pharmaceutical grade α-lactose monohydrate, sourced from DMV Fronterra Excipients, complying with the requirements of Ph.Eur/USNF may be used. Before use, the α-lactose monohydrate may be sieved through a coarse screen (for example with a mesh size 500 or 800 microns). The level of fines in the α-lactose monohydrate, which can be measured by Sympatec, may be 4.5% w/w less than 4.5 micron.

Compound (I) bromide is micronised before use in an APTM microniser to give a mass median diameter of 1 to 5 microns, such as 2 to 5 microns.

Pharmaceutical grade magnesium stearate, sourced from Peter Greven, complying with the requirements of Ph.Eur/USNF may be used as supplied with a mass median particle size, of 8 to 12 microns.

Blend A

Lactose monohydrate may be passed through a sieve and then combined with magnesium stearate and blended using either a high shear mixer (a QMM, PMA or TRV series mixer, such as TRV25 or TRV65) or a low shear tumbling blender (a Turbula mixer) to provide a magnesium stearate-lactose, premix, hereinafter referred to as blend A.

Blend B

Final blend B may be obtained as follows. An quantity of blend A and compound (I) bromide may be screened, for example using a COMIL™, and then blended with the remaining blend A using either a high shear Mixer (a QMM, PMA or TRV series mixer, such as TRV25 or TRVS5) or a low shear tumbling blender (a Turbula mixer).

Representative Batch Formula for Compound (I) Bromide Powder Blend (62.5 Microgram Per Blister)

| Ingredient | Quantity |
| --- | --- |
| Micronised Compound (I) Bromide | 74.1 g |
| Magnesium Stearate | 75 g |
| Lactose Monohydrate | To 12.5 kg |

Note: 74.1 g of Compound (I) Bromide is equivalent to 62.5 g of the free cation. The quantity of Compound (I) Bromide added may be adjusted to reflect the assigned purity of the input drug substance.

Representative Batch Formula for Compound (I) Bromide Powder Blend (125 Microgram Per Blister)

| Ingredient | Quantity |
| --- | --- |
| Micronised Compound (I) Bromide | 148.3 g |
| Magnesium Stearate | 75 g |
| Lactose Monohydrate | To 12.5 kg |

Note: 148.3 g of Compound (I) Bromide is equivalent to 125 g of the free cation. The quantity of Compound (I) Bromide added may be adjusted to reflect the assigned purity of the input drug substance.

Blending Parameters (using a TRV25, 12.5 kg Scale)

| Blend | Time (mins) | Approximate Speed (rpm) |
| --- | --- | --- |
| A | 6 | 460 |
| B | 10 | 590 |

Blister Strip Preparation

The blended composition may then be transferred into blister strips (typical nominal mean quantity of blend per blister is 12.5-13.5 mg) of the type generally used for the supply of dry powder for inhalation and the blister strips were sealed in the customary fashion.

Compound (II) Triphenylacetate

Pharmaceutical grade α-lactose monohydrate, which can be sourced from DMV Fronterra Excipients, complying with the requirements of Ph.Eur/USNF may be used. Before use, the α-lactose monohydrate may be sieved through a coarse screen (typical mesh size 500 microns). The level of fines in the α-lactose monohydrate, which can be measured by Sympatec, may be 4.5% w/w less than 4.5 micron.

Compound (II) triphenylacetate is micronised before use in an APTM microniser to give a MMD (mass median diameter) of from 1 to 5 microns, such as 2 to 5 microns, for example 1.8 microns.

Pharmaceutical grade Magnesium stearate, which can be sourced from Peter Greven, complying with the requirements of Ph.Eur/USNF may be used as supplied with a mass median particle size 8 to 12 microns.

Blend A

Lactose monohydrate may be passed through a sieve and then combined with magnesium stearate (typically 130 g) and blended using either a high shear mixer (a QMM, PMA or TRV series mixer, such as TRV25 car TRV65) or a low shear tumbling blender (a Turbula mixer) to provide a magnesium stearate/lactose premix, hereinafter referred to as blend A.

Blend B

Final blend B may be obtained as follows. An appropriate quantity of blend A and compound (II) triphenyiacetate (typically 5-165 g) may be screened, for example using a COMIC™, and then blended with the remaining blend A using either a high shear mixer (a QMM, PMA or TRV series mixer) or a low shear tumbling blender (a Turbula mixer). The final concentration of compound (II) triphenyiacetate in the blends is typically in the range 0.02% w/w-0.8% w/w free base equivalent.

Blister Strip Preparation

The blended composition is transferred into blister strips (typical nominal mean quantity of blend B per blister is 12.5-13.5 mg) or the type generally used for the supply of dry powder for inhalation and the blister strips are then sealed in the customary fashion.

Example Preparations

Using the above-described procedure the following exemplary formulations may be prepared:

| Blend No | Mass of Mass of Magnesium Stearate | Mass of Mass of compound (II) triphenylacetate (micronised) | Mass of lactose | Quantity per blister |
|---|---|---|---|---|
| 1 | 130 g | 5.0 g | To 13 kg | 13 mg |
| 2 | 130 g | 10.3 g | To 13 kg | 13 mg |
| 3 | 130 g | 20.7 g | To 13 kg | 13 mg |
| 4 | 130 g | 41.3 g | To 13 kg | 13 mg |
| 5 | 130 g | 82.7 g | To 13 kg | 13 mg |
| 6 | 130 g | 165.4 g | To 13 kg | 13 mg |

Note: The quantity of compound (II) triphenylacetate used is based on a base to salt conversion factor of 1.59. For example, 41 g of Compound (II) triphenylacetate is equivalent to 25 g of the free base.

Example Blending Parameters (using a TRV25, 13 kg Scale, Compound (II) Triphenylacetate Powder Blend (25 Microgram Blister))

| Blend | Time (mins) | Approximate Speed (rpm) |
|---|---|---|
| A | 9 | 550 |
| B | 8.5 | 550 |

Example Dry Powder Inhaler Devices

Compound (I) bromide and Compound (II) triphenylacetate as an inhalation powder may be administered in a DPI device containing two blister strips. One strip contains a blend of micronised Compound (I) bromide (approximately 500 micrograms per blister), magnesium stearate and lactose, monohydrate. The second strip contains a blend of micronised Compound (II) triphenylacetate (approximately 25 micrograms per blister), magnesium stearate and lactose monohydrate. The DPI device will deliver, when actuated, the contents of a single blister simultaneously from each of the two blister strips. Each blister strip is a double foil laminate containing 30 blisters per strip.

In a further embodiment, Compound (I) bromide and Compound (II) triphenylacetate as an inhalation powder may be administered in a dry powder inhaler device containing two blister strips, wherein one strip contains a blend of micronised Compound (I) bromide (approximately 125 or 62.5 micrograms per blister), magnesium stearate (at an amount of 0.6% w/w of the total powder weight per blister) and lactose monohydrate. The second strip contains a blend of micronised Compound (II) triphenylacetate (approximately 25 micrograms per blister), magnesium stearate and lactose monohydrate. The second strip optionally further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) at an amount of approximately 100 micrograms per blister. The DPI device will deliver, when actuated, the contents of a single blister simultaneously from each of the two blister strips. Each blister strip is a double foil laminate containing 7, 14 or 30 filled blisters per strip.

In a further embodiment, Compound (I) bromide and Compound (II) triphenylacetate as an inhalation powder may be administered in a dry powder inhaler device containing two blister strips, wherein one strip contains a blend of micronised Compound (I) bromide (approximately 125 or 62.5 micrograms per blister), Compound (II) triphenylacetate (approximately 25 micrograms per blister), magnesium stearate and lactose monohydrate. The second strip contains a blend of 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) at an amount of approximately 100 micrograms per blister, and lactose monohydrate. The DPI device will deliver, when actuated, the contents of a single blister simultaneously from each of the two blister strips. Each blister strip is a double foil laminate containing 7, 14 or 30 filled busters per strip.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

The invention claimed is:

1. A pharmaceutical combination product comprising
a) a compound of the formula

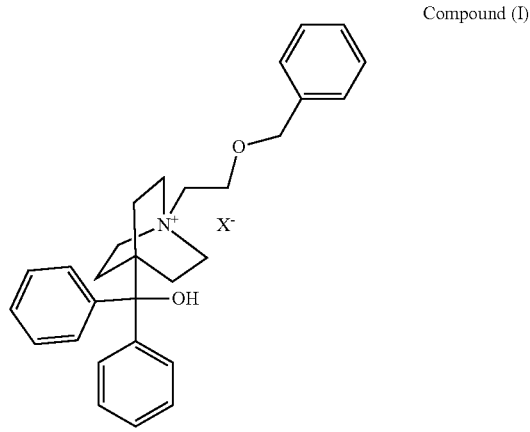

Compound (I)

wherein

X⁻ is a pharmaceutically acceptable anion wherein Compound (I) is in an amount of about 62.5 mcg/dose in the combination product, and is in the form of a dry powder; and b) 4-{(1R)-2-[(6-{2-[(2,6-dichlorobenzyl)oxy]ethoxy}hexyl)amino]-1-hydroxyethyl}-2-(hydroxymethyl)phenol, or a pharmaceutically acceptable salt thereof (Compound II), wherein Compound (II) is in an amount of about 25 mcg/dose in the combination product, and is in the form of a dry powder, wherein said pharmaceutical combination product is suitable for once daily administration, and wherein compounds (a) and (b) are presented in a form adapted for simultaneous administration.

2. The combination product according to claim 1, wherein for Compound (I) the pharmaceutically acceptable anion is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

3. The combination product according to claim 2, wherein Compound (I) is 4-[hydroxy(diphenyl)methyl]-1-{2-[(phenylmethyl)oxy]ethyl}-1-azoniabicyclo[2.2.2]octane bromide.

4. The combination product according to claim 1, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

5. The combination product according to claim 3, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

6. The combination product according to claim 1, wherein the pharmaceutical product is in a form suitable for administration by inhalation via a medicament dispenser, wherein said medicament dispenser is selected from the group consisting of a reservoir dry powder inhaler, a unit-dose dry powder inhaler, and a pre-metered multi-dose dry powder inhaler.

7. The combination product according to claim 6, wherein Compound (I) and Compound (II) are presented in (i) separate dry powder compositions or (ii) an admixed dry powder composition.

8. The combination product according to claim 7, wherein each separate dry powder composition or the admixed dry powder composition contains a carrier, which is lactose.

9. The combination product according to claim 8, wherein each separate or the admixed composition contains a ternary agent.

10. The combination product according to claim 9, wherein the ternary agent is magnesium stearate.

11. The combination product according to claim 7, wherein said separate or admixed composition is in unit dose form, and further wherein the unit dose form is selected from the group consisting of a capsule, a cartridge and a blister.

12. The combination product according to claim 1, wherein the pharmaceutical combination product further comprises 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

13. The combination product according to claim 12, wherein the 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

14. The combination product according to claim 5, wherein the pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

15. The combination product according to claim 14, wherein the 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

16. The combination product according to claim 5, wherein the pharmaceutical product is in a form suitable for administration by inhalation via a medicament dispenser, wherein said medicament dispenser is selected from the group consisting of a reservoir dry powder inhaler, a unit-dose dry powder inhaler, and a pre-metered multi-dose dry powder inhaler.

17. The combination product according to claim 16, wherein Compound (I) and Compound (II) are presented in (i) separate dry powder compositions or (ii) an admixed dry powder composition.

18. The combination product according to claim 17, wherein each separate dry powder composition or the admixed dry powder composition contains a carrier, which is lactose.

19. The combination product according to claim 18, wherein each separate or the admixed composition contains a ternary agent.

20. The combination product according to claim 19, wherein the ternary agent is magnesium stearate.

21. The combination product according to claim 17, wherein said separate or admixed compositions is in unit dose form, and further wherein the unit dose form is selected from the group consisting of a capsule, a cartridge and a blister.

22. A pharmaceutical combination product comprising
a) a first dry powder composition comprising:
(i) about 62.5 mcg/dose of a compound of the formula:

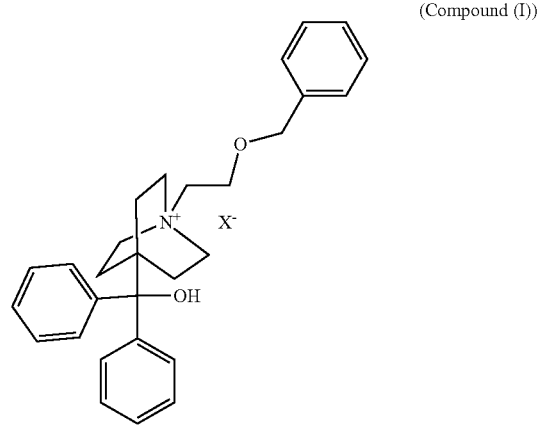

(Compound (I))

wherein X⁻ is a pharmaceutically acceptable anion;
(ii) lactose; and
(iii) magnesium stearate in an amount of about 0.6% w/w of said first dry powder composition; and
b) a second dry powder composition comprising:
(i) about 25 mcg/dose of 4-{(1R)-2-[(6-{2-[(2,6-dichlorobenzyl)oxy]ethoxy}hexyl)amino]-1-hydroxyethyl}-2-(hydroxymethyl)phenol, or a pharmaceutically acceptable salt thereof (Compound (II));
(ii) lactose; and
(iii) magnesium stearate in an amount of about 1.0% w/w of said second dry powder composition.

23. The combination product according to claim 22, wherein for Compound (I), the pharmaceutically acceptable anion is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

24. The combination product according to claim 23, wherein for Compound (I) the pharmaceutically acceptable anion is bromide.

25. The combination product according to claim 22, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

26. The combination product according to claim 24, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

27. The combination product according to claim 22, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

28. The combination product according to claim 23, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

29. The combination product according to claim 24, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

30. The combination product according to claim 25, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

31. A pharmaceutical combination product comprising
   a) a first dry powder composition comprising:
      (i) about 62.5 mcg/dose of a compound of the formula:

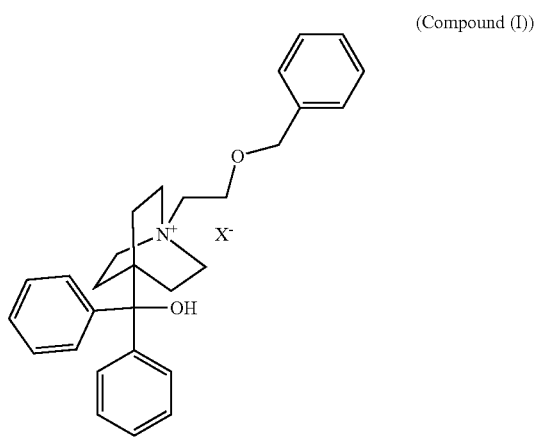

(Compound (I))

wherein X⁻ is a pharmaceutically acceptable anion;
      (ii) about 25 mcg/dose of 4-{(1R)-2-[(6-{2-[(2,6-dichlorobenzyl)oxy]ethoxy}hexyl)amino]-1-hydroxyethyl}-2-(hydroxymethyl)phenol, or a pharmaceutically acceptable salt thereof (Compound (II));
      (iii) carrier excipient; and
      (iv) a ternary agent, and
   b) a second dry powder composition comprising:
      (i) 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), present in an amount of about 100 mcg/dose; and
      (ii) carrier excipient.

32. The combination product according to claim 31, wherein for Compound (I), the pharmaceutically acceptable anion is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

33. The combination product according to claim 32, wherein for Compound (I) the pharmaceutically acceptable anion is bromide.

34. The combination product according to claim 31, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

35. The combination product according to claim 33, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

36. The combination product of claim 31, wherein the carrier excipient comprises lactose, and the ternary agent comprises magnesium stearate.

37. The combination product of claim 36, wherein the pharmaceutical combination product is administered via a medicament dispenser, wherein said medicament dispenser is selected from the group consisting of a reservoir dry powder inhaler, a unit-dose dry powder inhaler, and a pre-metered multi-dose dry powder inhaler.

38. The combination product according to claim 37, wherein each of said first and second dry powder compositions is in unit dose form, wherein said unit dose forms are independently selected from the group consisting of a capsule, a cartridge and a blister.

39. The combination product of claim 35, wherein the carrier excipient comprises lactose, and the ternary agent comprises magnesium stearate.

40. The combination product of claim 39, wherein the pharmaceutical combination product is administered via a medicament dispenser, wherein said medicament dispenser is selected from the group consisting of a reservoir dry powder inhaler, a unit-dose dry powder inhaler, and a pre-metered multi-dose dry powder inhaler.

41. The combination product according to claim 40, wherein each of said first and second dry powder compositions are in unit dose form, wherein said unit dose forms are independently selected from the group consisting of a capsule, a cartridge and a blister.

42. The combination product according to claim 9, wherein the ternary agent is magnesium stearate, present in an amount of about 0.6% w/w of a composition of Compound (I).

43. The combination product according to claim 9, wherein the ternary agent is magnesium stearate, present in an amount of about 1.0% w/w of a composition of Compound (II).

44. The combination product according to claim 9, wherein the ternary agent is magnesium stearate, present in an amount of about 0.6% w/w of a composition of Compound (I) and in an amount of about 1.0% w/w of a composition of Compound (II).

45. The combination product according to claim 19, wherein the ternary agent is magnesium stearate, present in an amount of about 0.6% w/w of a composition of Compound (I).

46. The combination product according to claim 19, wherein the ternary agent is magnesium stearate, present in an amount of about 1.0% w/w of a composition of Compound (II).

47. The combination product according to claim 19, wherein the ternary agent is magnesium stearate, present in an amount of about 0.6% w/w of a composition of Compound (I) and in an amount of about 1.0% w/w of a composition of Compound (II).

48. The combination product according to claim 19, wherein the pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

49. The combination product according to claim 48, wherein the fluticasone furoate is present in an amount of about 100 mcg/dose.

50. The combination product of claim 48, wherein the pharmaceutical combination product is administered via a medicament dispenser, wherein said medicament dispenser is selected from the group consisting of a reservoir dry powder inhaler, a unit-dose dry powder inhaler, and a pre-metered multi-dose dry powder inhaler.

51. The combination product according to claim 50, wherein Compound (I) and Compound (II) are presented in (i) separate dry powder compositions or (ii) an admixed dry powder composition.

52. The combination product according to claim 51, wherein each separate dry powder composition or the admixed dry powder composition contains a carrier, which is lactose.

53. The combination product according to claim 52, wherein each separate or the admixed composition contains a ternary agent.

54. The combination product according to claim 53, wherein the ternary agent is magnesium stearate.

55. The combination product according to claim 54, wherein the magnesium stearate is present in a composition comprising Compound (II), in an amount of about 1.0% w/w of the composition comprising Compound (II).

56. The combination product according to claim 50, wherein said dry powder compositions are in unit dose form, wherein each of said unit dose forms are independently selected from the group consisting of a capsule, a cartridge or a blister.

\* \* \* \* \*